United States Patent [19]
Burt et al.

[11] Patent Number: 5,493,016
[45] Date of Patent: Feb. 20, 1996

[54] PROCESSES FOR THE PREPARATION OF ALKOXY-BRIDGED METALLOPHTHALOCYANINE DIMERS

[75] Inventors: Richard A. Burt, Oakville; George Liebermann; Gordon K. Hamer, both of Mississauga; Sandra J. Gardner, Willowdale; Carol A. Jennings, Mississauga, all of Canada; Katsumi Daimon; Katsumi Nukada, both of Minami, Japan

[73] Assignee: Xerox Corporation, Stamford, Conn.

[21] Appl. No.: 233,195

[22] Filed: Apr. 26, 1994

[51] Int. Cl.[6] .................................................. C07D 487/22
[52] U.S. Cl. .......................... 540/139; 540/140; 540/142; 540/143
[58] Field of Search ................... 540/139, 140, 540/142, 143

[56] References Cited

U.S. PATENT DOCUMENTS

| | | | |
|---|---|---|---|
| 5,039,798 | 8/1991 | Johnson | 540/139 |
| 5,164,493 | 11/1992 | Mayo et al. | 540/143 |
| 5,334,714 | 8/1994 | Oguchi et al. | 540/143 |
| 5,437,929 | 8/1995 | Kenney et al. | 540/139 |
| 5,446,142 | 8/1995 | Itoh et al. | 540/122 |

FOREIGN PATENT DOCUMENTS

| | | |
|---|---|---|
| 0136036 | 11/1978 | Japan. |
| 1221459 | 9/1984 | Japan. |
| 5-263007 | 10/1993 | Japan. |

OTHER PUBLICATIONS

Organic Chemistry, By Morrison and Boyd Allyn and Bacon; Fifth Editon., 1987 p. 178.
Bull. Soc. Chim. Fr., 23 (1962), D. Colaitis.
J. Chem. Soc., 1717, 1936, P. A. Barrett et al.
Inorg. Chem., 25, 3972, 1986, C. Ercolani et al.
Inorg. Chem. 12, 930, 1973, W. R. Bennett et al.

*Primary Examiner*—Mukund J. Shah
*Assistant Examiner*—Pavanaram K. Sripada
*Attorney, Agent, or Firm*—E. O. Palazzo

[57] ABSTRACT

A process for the preparation of alkoxy-bridged metallophthalocyanine dimers by the reaction of a trivalent metal compound with ortho-phthalodinitrile or 1,3-diiminoisoindoline in the presence of a diol.

36 Claims, 6 Drawing Sheets

PROCESSES FOR THE PREPARATION OF ALKOXY-BRIDGED METALLOPHTHALOCYANINE DIMERS

BACKGROUND OF THE INVENTION

This invention is generally directed to processes for the preparation of alkoxy-bridged metallophthalocyanine dimers, such as alkoxy-bridged metallophthalocyanine dimers of a trivalent metal of the Formula

FORMULA 1

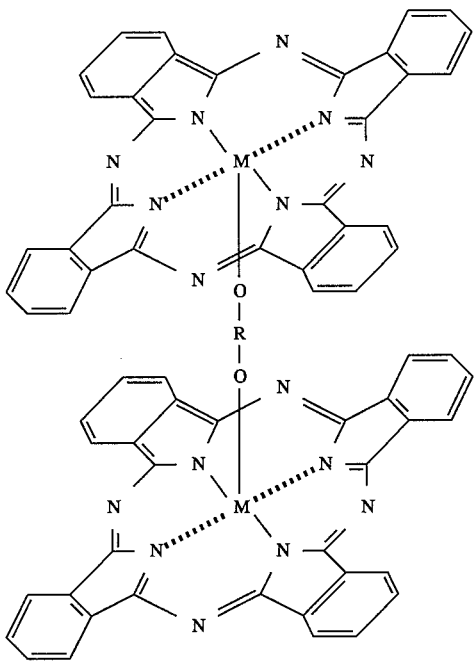

wherein M is a trivalent metal, and R is an alkyl group or an alkyl ether group, reference copending patent application U.S. Ser. No. 239,432 the disclosure of which is totally incorporated herein by reference.

The alkoxy-bridged metallophthalocyanine dimers of Formula 1 are believed to be novel phthalocyanine dimers, or diphthalocyanines characterized by an alkoxy (—O—R—O) bridge between the two metallophthalocyanine rings. The structure between the two oxygen molecules of the bridge is determined by the diol used in the synthesis: The trivalent metal in the phthalocyanine dimer structure can be aluminum, gallium or indium, or trivalent transitional metals, such as Mn(III), Fe(III), Co(III), Ni(III), Cr(III), and the like.

In embodiments, the present invention is directed to processes for the preparation of specific alkoxy-bridged metallophthalocyanine dimers, including alkoxy-bridged gallium phthalocyanine dimers. More specifically, the present invention in embodiments is directed to processes for the preparation of alkoxy bridged metallophthalocyanine dimers directly from known phthalocyanine precursors such as orthophthalodinitrile or 1,3-diiminoisoindoline. The alkoxy-bridged metallophthalocyanine dimers can be obtained by the reaction of orthophthalodinitrile or 1,3-diiminoisoindoline with a trivalent metal alkoxide and a diol. During the aforementioned reaction, the diol, which can act also as a solvent for the reaction, is chemically incorporated into the phthalocyanine product enabling the formation of an alkoxy-bridged metallophthalocyanine dimer of Formula 1 $C_{32}H_{16}N_8MOROMN_8H_{16}C_{32}$ wherein M is a trivalent metal and the alkoxy bridge O—R—O) contains an alkyl group, such as ethyl, propyl or butyl, which originates from the diol selected.

The alkoxy-bridged metallophthalocyanine dimers can also be obtained by the reaction of ortho-phthalodinitrile or 1,3-diiminoisoindoline with other complexes of trivalent metals, such as the triacetates, for example gallium acetate, and the triacetylacetonates, such as gallium acetylacetonate, and a diol.

Processes for the preparation of alkoxy-bridged metallophthalocyanine dimers can also be accomplished when the trivalent metal alkoxide is not readily available or stable by preparing the trivalent metal alkoxide as part of the phthalocyanine synthesis, and selecting the freshly prepared metal alkoxide for the reaction with orthophthalodinitrile or 1,3-diiminoisoindoline, and a diol to form the alkoxy-bridged metallophthalocyanine dimer.

In embodiments, the present invention is also directed to an efficient and economical process for the preparation of alkoxy-bridged metallophthalocyanine dimers by the in situ formation of trivalent metal alkoxides from metal halides. The metal halides are about one-tenth the cost and readily available from sources like certain United States corporations (such as APL Engineered Materials, Urbana, Ill., and Gallard-Schlesinger Industries, Carle Place, N.Y.) which supply inorganic or organometallic chemicals on multikilogram scale from stock supplies, compared to the corresponding trivalent metal alkoxides, acetates and acetylacetonates, which are usually considered special order components and which are generated on less than one kilogram scale. Thus, the alkoxy-bridged metallophthalocyanine dimers of the present invention can be prepared in efficient, economical and high yield, for example about 70 to about 85 percent, from metal halides.

Alternatively, the alkoxy-bridged metallophthalocyanine dimers can be prepared by first preparing a halometallo phthalocyanine of a trivalent metal, which is then hydrolyzed to the corresponding hydroxymetallo phthalocyanine. The hydroxymetallo phthalocyanine can be converted to an alkoxy-bridged metallophthalocyanine dimer by reaction with a diol in the presence of excess diol or another solvent.

In embodiments, the present invention relates to processes for obtaining alkoxy-bridged gallium phthalocyanines as representatives of a new class of alkoxy-bridged metallophthalocyanine dimers of Formula 1.

The alkoxy-bridged metallophthalocyanine dimers obtained with the processes of the present invention, such as alkoxy-bridged gallium phthalocyanine dimers, can be selected as photogenerator components in photoresponsive or photoconductive imaging members reference copending patent applications U.S. Ser. No. 239,432 and U.S. Ser. No. 233,834 the disclosures of which are totally incorporated herein by reference. These imaging members may be layered photoconductive imaging members, and may contain separate charge transport layers, especially hole transport layers containing hole transport molecules. The imaging members containing alkoxy-bridged metallophthalocyanine dimers possess infrared photosensitivity, and are sensitive in the wavelength regions of from about 650 to about 850 nanometers, therefore, diode lasers can be selected as the light source. The layered photoconductive imaging members can be selected for a number of different known imaging and printing processes including, for example, electrophotographic imaging processes, especially xerographic imaging and printing processes wherein negatively charged or positively charged images are rendered visible using toner compositions of appropriate charge polarity. The alkoxy-bridged metallophthalocyanine dimers can be used as precursors for the preparation of other phthalocyanines such as hydroxy metallophthalocyanines, which phthalocyanines may be selected as the photogenerating pigment in photoresponsive imaging members. Further, the alkoxy-bridged metallophthalocyanines obtained with the processes of the present invention can also be selected as precursors for the preparation of other phthalocyanine compounds, such as hydroxymetallo phthalocyanines, for example hydroxygallium phthalocyanine, as described in copending application U.S. Ser. No. (not yet assigned D/93606).

Certain metallophthalocyanines containing two phthalocyanine rings in the molecule have been described in the literature. Early work by P. A. Barrett et al. in *J. Chem Soc.*, 1717, 1936 cites the discovery of (AlPc)$_2$O, a μ-oxo bridged aluminum phthalocyanine of Formula 2.

FORMULA 2

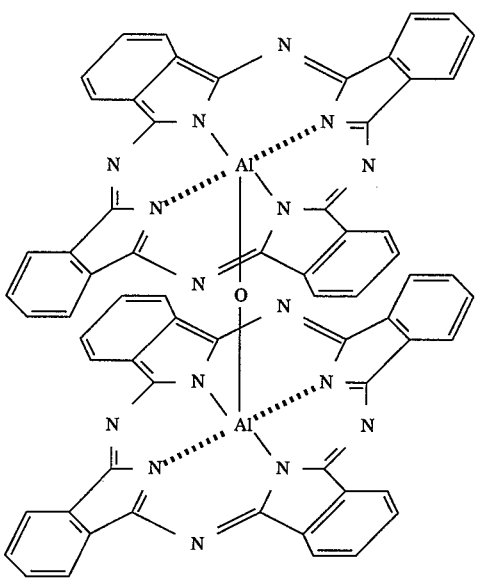

The formation of a similar compound of trivalent Fe, (Fe Pc)$_2$O by aeration of FePc was described by C. Ercolani et al. in *Inorg. Chem.*, 25, 3972, 1986.

Bis(phthalocyaninato)lanthanide(III) complexes, also described as lanthanide diphthalocyanines [L(Pc)$_2$] have been reported by I. S. Kirin et al. in Russ. *J. Phys. Chem* (Engl Transl), 41, 251, 1967. The lutetium phthalocyanine dimer has been reviewed in the literature, for example for its electrochromic properties. *Phthalocyanines Properties and Applications*, 1989, VCH Publishers, Inc., edited by C. C. Leznoff and A. B. P. Lever, describes a series of these materials, with the corresponding original references.

Diphthalocyanines of tetravalent metals, such as stanium, Sn(Pc)$_2$, and zirconium, Zr(Pc)$_2$, of the structure shown in Formula 3, have been synthesized and described by W. R. Bennet et al. in *Inorg Chem.*, 12, 930, 1973 and J. Silver et al. in *Polyhedron*, 8, 1631, 1989.

FORMULA 3

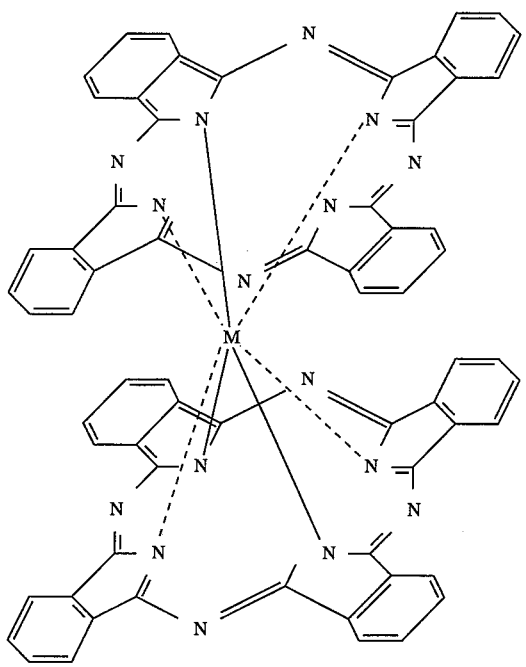

wherein M is a metal.

In the aforementioned documents, there is believed to be no disclosure of alkoxy-bridged metallophthalocyanine dimers, such as alkoxy-bridged gallium phthalocyanine dimers, or processes for the preparation thereof.

Many halometallo- and hydroxymetallo phthalocyanines of trivalent metals, such as Al, Ga and In, are disclosed in the literature, for example in *The Phthalocyanines*, vol. I and II, F. H. Moser and A. L. Thomas, CRC Press Inc., 1983 and by J. P. Linsky et al. in *Inorg. Chem.* 19, 3131, 1980.

In *Bull. Soc. Chim. Fr.*, 23 (1962), there is illustrated the preparation of chlorogallium phthalocyanine by the reaction of o-cyanobenzamide with gallium chloride in the absence of solvent, and hydroxygallium phthalocyanine by dissolution of chlorogallium phthalocyanine in concentrated sulfuric acid, followed by reprecipitation in diluted aqueous ammonia. Further, there are illustrated in JPLO 1-221459 (Toyo Ink Manufacturing) processes for preparing chlorogallium phthalocyanines and hydroxygallium phthalocyanines as well as photoreceptors for use in electrophotography. A number of hydroxygallium phthalocyanine polymorphs and processes for the preparation thereof are described in JPLO 5-263007, the disclosure of which is totally incorporated herein by reference.

More specifically, in *Bull. Soc. Chim. Fr.*, 23 (1962) there is illustrated the preparation of hydroxygallium phthalocyanine via the precursor chlorogallium phthalocyanine. The precursor chlorogallium phthalocyanine is prepared by reaction of o-cyanobenzamide with gallium chloride in the absence of solvent. o-Cyanobenzamide is heated to its melting point (172° C.), and to it is added gallium chloride, at which time the temperature is increased to 210° C. for 15 minutes, and then cooled. The solid is recrystallized out of boiling chloronaphthalene to provide purple crystals having carbon, hydrogen and chlorine analyses matching theoretical values for chlorogallium phthalocyanine. Dissolution in concentrated sulfuric acid, followed by reprecipitation in diluted aqueous ammonia, affords material having carbon and hydrogen analyses matching theoretical values for hydroxygallium phthalocyanine. Further, in JPLO 221459 a photoreceptor for use in electrophotography, comprising a charge generation material and charge transport material on a conductive substrate, and the charge generation material comprising one or a mixture of two or more of gallium phthalocyanine compounds which show the following intense diffraction peaks at Bragg angles (2 theta +/–0.2°) in the X-ray diffraction spectrum, 1—6.7, 15.2, 20.5, 27.0
2—6.7, 13.7, 16.3, 20.9, 26.3
3—7.5, 9.5, 11.0, 13.5, 19.1, 20.3, 21.8, 25.8, 27.1, 33.0.

Hydroxygallium phthalocyanine is generally obtained by the hydrolysis of chlorogallium phthalocyanine. Ring chlorination often occurs in the preparation of chlorogallium phthalocyanine as gallium chloride is used at high temperature in the synthesis, which can effect the purity of the final product. These detrimental characteristics can result in detrimental properties when the phthalocyanine is used for high purity applications such as electrophotography. This can be avoided or minimized by using the alkoxy-bridged gallium phthalocyanine dimers of the present invention as the precursor. The alkoxy-bridged gallium phthalocyanine dimer can be hydrolyzed to hydroxygallium phthalocyanine by treatment with sulfuric acid using a procedure similar to that described for the hydrolysis of chlorogallium phthalocyanine in *Bull. Soc. Chim. Fr.*, 23 (1962). The hydroxygallium phthalocyanine can then be converted to the photosensitive Type V hydroxygallium phthalocyanine polymorph as described in copending application U.S. Ser. No. 233,834 the disclosure of which is totally incorporated herein by reference. By selecting an alkoxy-bridged gallium phthalocyanine dimer precursor in the preparation of Type V hydroxygallium phthalocyanine, any negative effects of residual chlorine, or ring chlorination, such as higher dark decay and higher cycledown, are avoided or minimized.

Imaging member applications of alkoxy-bridged metallophthalocyanine dimers, including their use as photogenerator pigments in electrophotographic devices, require commercially viable processes in which the alkoxy-bridged metallophthalocyanine dimers are obtained in high purity, acceptable yields, and with superior electrophotographic properties.

In Konica Japanese 64-17066/89, there is disclosed, for example, the use of a new crystal modification of titanyl phthalocyanine (TiOPc) prepared from alpha-type TiOPc (Type II) by milling it in a sand mill with salt and polyethylene glycol. This publication also discloses that this new polymorph differs from alpha-type pigment in its light absorption and shows a maximum absorbance at 817 nanometers while the alpha-type exhibits a maximum at 830 nanometers. The Konica publication also discloses the use of this new form of TiOPc in a layered electrophotographic device having high photosensitivity at exposure radiation of 780 nanometers. Further, this new polymorph of TiOPc is also described in U.S. Pat. No. 4,898,799 and in a paper presented at the Annual Conference of Japan Hardcopy in July 1989. In this paper, this same new polymorph is referred to as Type Y, and reference is also made to Types I, II, and III as A, B, and C, respectively. Also, in U.S. Ser. No. 169,486, the disclosure of which is totally incorporated herein by reference, there is illustrated a process for the preparation of hydroxygallium phthalocyanine Type V, essentially free of chlorine, whereby a pigment precursor Type I chlorogallium phthalocyanine is prepared by reaction of gallium chloride in a solvent, such as N-methylpyrrolidone, present in an amount of from about 10 parts to about 100 parts, and preferably about 19 parts with 1,3-diiminoisoindoline (DI$^3$) in an amount of from about 1 part to about 10 parts, and preferably about 4 parts of DI$^3$ for each part of gallium chloride that is reacted; hydrolyzing said pigment precursor chlorogallium phthalocyanine Type I by standard methods, for example acid pasting, whereby the pigment precursor is dissolved in concentrated sulfuric acid and then reprecipitated in a solvent, such as water, or a dilute ammonia solution, for example from about 10 to about 15 percent; and subsequently treating the resulting hydrolyzed pigment hydroxygallium phthalocyanine Type I with a solvent, such as N,N-dimethylformamide, present in an amount of from about 1 volume part to about 50 volume parts and preferably about 15 volume parts, for each weight part of pigment hydroxygallium phthalocyanine that is used by, for example, ball milling said Type I hydroxygallium phthalocyanine pigment in the presence of spherical glass beads, approximately 1 millimeter to 5 millimeters in diameter at room temperature, about 25° C., for a period of from about 12 hours to about 1 week, and preferably about 24 hours such that there is obtained a hydroxygallium phthalocyanine Type V, which contains very low levels of residual chlorine of from about 0.001 percent to about 0.1 percent, and in an embodiment about 0.03 percent of the weight of the Type V hydroxygallium pigment, as determined by elemental analysis.

Further in U.S. Pat. No. 5,407,766 disclosure of which is totally incorporated herein by reference, there is illustrated a process for the preparation of hydroxygallium phthalocyanine Type V, which comprises formation of a precursor of gallium phthalocyanine, prepared by reaction of 1,3-diiminoisoindoline with gallium acetylacetonate in a suitable solvent solvent; hydrolyzing the precursor by dissolving in a strong acid and then reprecipitating the dissolved pigment in aqueous ammonia, thereby forming Type I hydroxygallium phthalocyanine; and admixing the Type I hydroxygallium phthalocyanine with a polar aprotic organic solvent; and more specifically a process for the preparation of Type V hydroxygermanium phthalocyanine which comprises preparing a precursor gallium phthalocyanine by the reaction of 1,3-diiminoisoindoline with gallium acetylacetonate in a suitable solvent; filtering and, thereafter, washing the pigment precursor gallium phthalocyanine with hot N,N-dimethylformamide, followed by washing with an organic solvent, such as methanol, or acetone; hydrolyzing said precursor by dissolving in a strong acid and then reprecipitating the dissolved pigment in aqueous ammonia, thereby forming Type I hydroxygallium phthalocyanine; and admixing the Type I with the organic solvent N,N-dimethylformamide.

In the following copending patent applications filed concurrently herewith there is illustrated: U.S. Ser. No. 239,432 akoxy-bridged metallophthalocyanine dimers of the formula $C_{32}H_{16}N_8MOROMN_8H_{16}C_{32}$, or of the formula

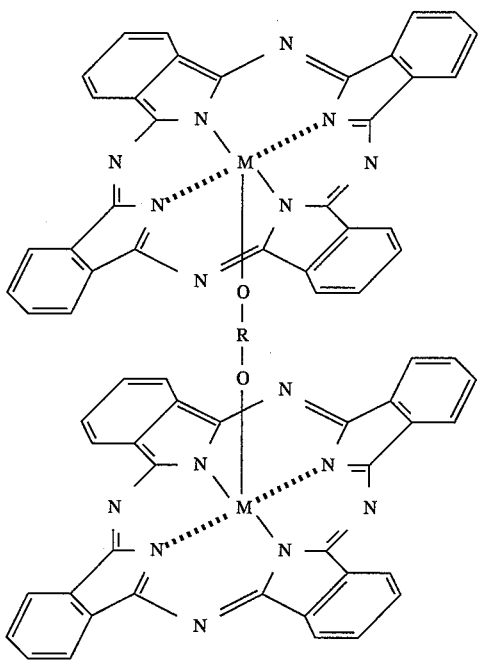
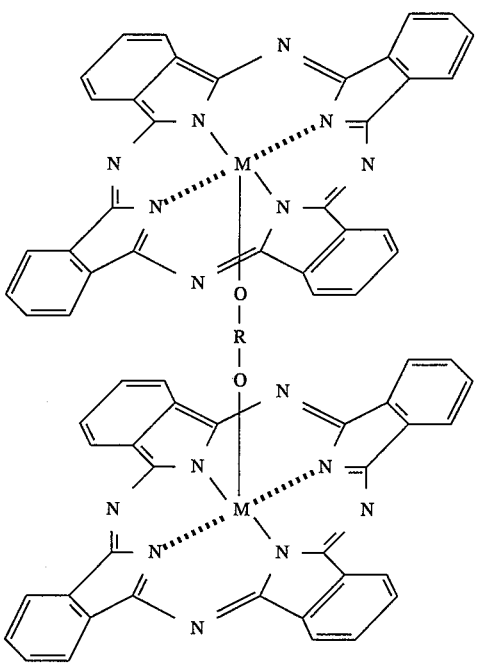

wherein M is a metal, and R is an alkyl or an alkyl ether; U.S. Ser. No. 233,834 a process for the preparation of Type V hydroxygallium phthalocyanine which comprises the in situ formation of an alkoxy-bridged gallium phthalocyanine dimer, hydrolyzing said alkoxy-bridged gallium phthalocyanine dimer to hydroxygallium phthalocyanine, and subsequently converting the hydroxygallium phthalocyanine product obtained to Type V hydroxygallium phthalocyanine; a process for the preparation of Type V hydroxygallium phthalocyanine which comprises the formation of an alkoxy-bridged gallium phthalocyanine dimer by the reaction of an organic gallium complex with ortho-phthalodinitrile or 1,3-diiminoisoindoline and a diol; hydrolyzing the resulting alkoxy-bridged gallium phthalocyanine dimer to hydroxygallium phthalocyanine, and subsequently converting the hydroxygallium phthalocyanine product obtained to Type V hydroxygallium phthalocyanine; U.S. Ser. No. 233,832 a photoconductive imaging member comprised of an alkoxy-bridged metallophthalocyanine dimer as a charge generator material, wherein the dimer is of the formula $C_{32}H_{16}N_8MOROMN_8H_{16}C_{32}$ wherein M is a trivalent metal, and R is an alkyl group or an alkyl ether group The disclosures of all of the aforementioned publications, laid open applications, copending applications and patents are totally incorporated herein by reference.

SUMMARY OF THE INVENTION

It is an object of the present invention to provide processes for the preparation of alkoxy-bridged metallophthalocyanine dimers with many of the advantages illustrated herein.

It is another object of the present invention to provide processes for the preparation of a new class of phthalocyanines referred to as alkoxy-bridged metallophthalocyanine dimers.

It is yet another object of the present invention to provide processes for the preparation of alkoxy-bridged metallophthalocyanine dimers useful as a precursor in the preparation of other polymorphs or other phthalocyanines such as hydroxygallium phthalocyanine Type V.

A further object of the present invention is to provide economically feasible processes for the synthesis of alkoxy-bridged metallophthalocyanine dimers in high yields.

Another object of the present invention is to provide processes for the synthesis of alkoxy-bridged metallophthalocyanine dimers of the formula $C_{32}H_{16}N_8MOROMN_8H_{16}C_{32}$, wherein M is a trivalent metal such as aluminum, gallium, indium, or other metals in a trivalent form such as Mn(III), Fe(III), Co(III), Ni(III), Cr(III), and the like, and R is an alkyl group or an alkyl ether.

It is another object of the present invention is to provide processes for the synthesis of alkoxy-bridged metallophthalocyanine dimers of the formula $C_{32}H_{16}N_8MOROMN_8H_{16}C_{32}$, wherein R is a moiety provided by the diol used in the preparation of the phthalocyanine dimer.

A further object of the present invention is to provide processes for the synthesis of alkoxy-bridged gallium phthalocyanine dimers of the formula $C_{32}H_{16}N_8GaOROGaN_8H_{16}C_{32}$, wherein R is a moiety provided by the diol used in the preparation of the phthalocyanine dimer.

A further object of the present invention is to provide processes for the synthesis of alkoxy-bridged gallium phthalocyanine dimers of the formulas $C_{32}H_{16}N_8GaOCH_2CH_2OGaN_8H_{16}C_{32}$, $C_{32}H_{16}N_8GaOCH(CH_3)CH_2OGaN_8H_{16}C_{32}$, $C_{32}H_{16}N_8GaOCH_2CH_2CH_2OGaN_8H_{16}C_{32}$ and $C_{32}H_{16}N_8GaOCH_2CH_2CH_2CH_2OGaN_8H_{16}C_{32}$.

Moreover, it is an object of the present invention to provide processes for the preparation of alkoxy-bridged metallophthalocyanine dimers by reacting trivalent metal complexes, such as alkoxides, acetates, or acetylacetonates, with known phthalocyanine precursors such as orthophthalodinitrile or 1,3-diiminoisoindoline in the presence of a diol.

In a further object of the present invention there are provided processes for the preparation of alkoxy-bridged metallophthalocyanine dimers in which trivalent metal alkoxides are prepared from the corresponding metal trihalide prior to the phthalocyanine synthesis step, and, thereafter, selected without isolation in the synthesis of alkoxy-bridged metallophthalocyanine dimers.

Another object of the present invention is to provide an economical one step in situ process for the preparation of alkoxy-bridged metallophthalocyanine dimers from commercially readily available metal trihalides.

Another object of the present invention is to provide simple and economical processes for the preparation of alkoxy-bridged gallium phthalocyanine dimers.

A further object of the present invention relates to the preparation of electrically pure, for example 99.0 to 99.95 percent pure, alkoxy-bridged metallophthalocyanine dimers in excellent yield, for example from about 30 percent to about 90 percent, and in embodiments about 80 percent.

Additionally, in another object of the present invention there is provided a two step process for the preparation of alkoxy-bridged metallophthalocyanine dimers and imaging members thereof.

In yet a further object of the present invention there is provided a one step in situ process for the preparation of alkoxy-bridged metallophthalocyanine dimers.

In a further object of the present invention there are provided processes for the preparation of trivalent metal alkoxides from the metal halide, especially chloride thereof, for use in the synthesis of alkoxy-bridged metallophthalocyanine dimers, wherein the use of the trivalent metal chloride directly for the phthalocyanine synthesis is avoided, and which metal alkoxides can be selected as a reactant for the processes of the present invention either in situ or in a two step reaction.

DESCRIPTION OF THE EMBODIMENTS

These and other objects of the present invention can be accomplished in embodiments thereof by the provision of processes for the preparation of alkoxy-bridged metallophthalocyanine dimers. For example, in embodiments of the present invention there are provided processes for the preparation of alkoxy-bridged gallium phthalocyanine dimers by the reaction of a trivalent metal alkoxide like gallium alkoxide with ortho-phthalodinitrile or 1,3-diiminoisoindoline, and a diol. The alkoxy-bridged gallium phthalocyanine dimer formed is of the general formula as illustrated herein and, more specifically, $C_{32}H_{16}N_8GaOROGaN_8H_{16}C_{32}$ with, for example, from 2 to about 12, and preferably about 2 to 6 carbon atoms in the alkoxy bridge O—R—O). Embodiments of the present invention are directed to the preparation of alkoxy-bridged gallium phthalocyanine dimers, which comprise the dissolution of 1 part of a gallium trihalide, and preferably gallium trichloride in about 1 part to about 100 parts, and preferably about 10 parts of an organic solvent, such as benzene, toluene, xylene or the like, at a temperature of from about 0° C. to about 100° C., and preferably at a temperature of about 25° C. to form a solution of the gallium trichloride; followed by the addition of 3 parts of an alkali metal alkoxide, such as sodium methoxide, sodium ethoxide, sodium propoxide or the like, preferably in a solution form to provide a gallium alkoxide solution, and an alkali metal salt byproduct, for example sodium chloride, at a temperature of from about 0° C. to about 100° C., and preferably at a temperature of about 20° C. to about 40° C.; followed by the reaction with from about 1 part to about 10 parts, and preferably about 4 parts of ortho-phthalodinitrile or 1,3-diiminoisoindoline, and a diol, such as 1,2-ethanediol (ethylene glycol), 1,2-propanediol (propylene glycol) or 1,3-propanediol, in an amount of from about 3 parts to about 100 parts, and preferably about 10 parts for each part of the gallium alkoxide formed at a temperature of from about 150° C. to about 220° C., and preferably at a temperature of 195° C. for a period of 30 minutes to 6 hours, and preferably about 2 hours to provide an alkoxy-bridged gallium phthalocyanine dimer, which pigment is isolated by filtration at a temperature of about 20° C. to about 180° C., and preferably at about 120° C. to give a dark blue solid identified by elemental analysis, infrared spectroscopy, proton NMR spectroscopy and XRD.

In further embodiments of the present invention, there are provided processes for the preparation of alkoxy-bridged gallium phthalocyanine dimers by the reaction of gallium triacetate or gallium triacetylacetonate with ortho-phthalodinitrile or-1,3-diiminoisoindoline, and a diol. The alkoxy-bridged gallium phthalocyanine dimer formed is of the general Formula 1, or more specifically $C_{32}H_{16}N_8GaOROGaN_8H_{16}C_{32}$ with, for example, from about 2 to about 12, and preferably about 2 to about 6 carbon atoms in the alkoxy bridge O—R—O). Embodiments of the present invention are directed to the preparation of alkoxy-bridged gallium phthalocyanine dimers, which comprise the reaction of 1 part of gallium acetate or gallium acetylacetonate with from about 1 part to about 10 parts, and preferably about 4 parts of ortho-phthalodinitrile or 1,3-diiminoisoindoline, and a diol, such as 1,2-ethanediol (ethylene glycol), 1,2-propanediol (propylene glycol) or 1,3-propanediol, in an amount of from about 3 parts to about 100 parts, and preferably about 10 parts for each part of the gallium compound used at a temperature of from about 150° C. to about 220° C., and preferably at a temperature of 195° C. for a period of 30 minutes to 6 hours, and preferably about 2 hours to provide an alkoxy-bridged gallium phthalocyanine dimer, which pigment is isolated by filtration at a temperature of about 20° C. to about 180° C., and preferably at about 120° C. to provide a dark blue solid identified by elemental analysis, infrared spectroscopy, proton NMR spectroscopy and XRD.

In embodiments, a trivalent metal alkoxide, which alkoxide can contain from about 3 to about 54, and preferably from about 3 to about 24 carbon atoms can be obtained from the reaction of the corresponding metal trihalide with an alkali metal salt of an alcohol, such as sodium ethoxide, in a solvent. The formed trivalent metal alkoxide can be separated from the alkali metal halide byproduct by filtration, or the mixture may be utilized in situ in the subsequent reaction to form the alkoxy-bridged metallophthalocyanine dimer.

The trivalent metal alkoxide can also be obtained from the reaction of the corresponding metal trihalide with an alcohol in the presence of a base, such as ammonia, and a solvent. The formed trivalent metal alkoxide can be separated from the ammonium halide byproduct by filtration, or the mixture may be utilized in situ in the subsequent reaction to form the alkoxy-bridged metallophthalocyanine dimers. Embodiments of the present invention are directed to the preparation of alkoxy-bridged gallium phthalocyanine dimers, which comprise the dissolution of 1 part of a gallium trihalide, and preferably gallium trichloride in about 1 part to about 100 parts, and preferably about 10 parts of an organic solvent such as benzene, toluene, xylene or the like at a temperature of from about 0° C. to about 100° C., and preferably at a temperature of about 25° C. to form a solution of the gallium trichloride; followed by the addition of an aliphatic alcohol, such as ethanol or butanol, in about 1 part to about 10 parts, and preferably about 3 parts (by weight); followed by the addition of 3 parts of an amine, such as ammonia or triethylamine or the like, at a temperature of from about 0° C. to about 60° C., and preferably at a temperature of about 25° C. to provide a gallium alkoxide solution and an ammonium halide salt byproduct, for example ammonium chloride; followed by the reaction with from about 1 part to about 10 parts, and preferably about 4 parts of orthophthalodinitrile or 1,3-diiminoisoindoline, and a diol, such as 1,2-ethanediol (ethylene glycol), 1,2-propanediol (propylene glycol) or 1,3-propanediol, in an amount of from about 3 parts to about 100 parts, and preferably about 10 parts for each part of the gallium alkoxide formed at a temperature of from about 150° C. to about 220° C., and preferably at a temperature of 195° C. for a period of 30 minutes to 6 hours, and preferably about 2 hours to provide an alkoxy-bridged gallium phthalocyanine dimer, which dimer pigment is isolated by filtration at a temperature of about 20° C. to about 180° C., and preferably at about 120° C. to give a dark blue solid identified by elemental analysis, infrared spectroscopy, proton NMR spectroscopy and XRD.

In embodiments, the gallium alkoxide can be prepared by reacting a gallium trihalide, especially the trichloride, with an alkali metal alkoxide, and, thereafter, reacting the resulting gallium alkoxide with, for example, ortho-phthalodinitrile or 1,3-diiminoisoindoline, and a dialcohol (diol) to form the alkoxy-bridged gallium phthalocyanine dimers. The diol may also serve as a reaction solvent, or an organic solvent, such as N-methylpyrrolidone; halonaphthalenes like 1-chloronaphthalene; quinoline, and the like may be selected. Further, embodiments of the present invention are directed to the preparation of alkoxy-bridged gallium phthalocyanine dimers, which comprise the dissolution of 1 part of a gallium trihalide, and preferably gallium trichloride, in about 1 part to about 100 parts, and preferably about 10 parts of an organic solvent, such as benzene, toluene, xylene or the like, at a temperature of from about 0° C. to about 100° C., and preferably at a temperature of about 25° C. to form a solution of the gallium trichloride; followed by the addition of 3 parts of an alkali metal alkoxide, such as sodium methoxide, sodium ethoxide, sodium propoxide or the like, preferably in a solution form to provide a gallium alkoxide solution, and an alkali metal salt byproduct, for example sodium chloride, at a temperature of from about 0° C. to about 100° C., and preferably at a temperature of about 20° C. to about 40° C.; followed by the reaction with from about 1 part to about 10 parts, and preferably about 4 parts of ortho-phthalodinitrile or 1,3-diimiinoisoindoline, and a diol, such as 1,2-ethanediol (ethylene glycol), 1,2-propanediol (propylene glycol) or 1,3-propanediol, in an amount of from about 1 part to about 20 parts, and preferably about 5 parts for each part of the gallium alkoxide formed, and an additional organic solvent, such as N-methylpyrrolidone, a halonaphthalene like 1-chloronaphthalene, quinoline, and the like, in an amount of from about 5 parts to about 20 parts, and preferably about 10 parts at a temperature of from about 150° C. to about 220° C., and preferably at a temperature of 195° C. for a period of 30 minutes to 6 hours, and preferably about 2 hours to provide an alkoxy-bridged gallium phthalocyanine dimer, which dimer photogenerating pigment is isolated by filtration at a temperature of about 20° C. to about 180° C., and preferably at about 120° C. to give a dark blue solid identified by elemental analysis, infrared spectroscopy, proton NMR spectroscopy and XRD.

In embodiments, the gallium alkoxide can be prepared by reacting gallium trichloride with a sodium alkoxide, such as methoxide or ethoxide, and, thereafter, reacting the resulting gallium alkoxide with, for example, ortho-phthalodinitrile or 1,3-diiminoisoindoline, and a dialcohol (diol) to form the alkoxy-bridged gallium phthalocyanine dimers. Other embodiments of the present invention are directed to the preparation of alkoxy-bridged gallium phthalocyanine dimers, which comprise the dissolution of 1 part of gallium trichloride, in about 1 part to about 100 parts, and preferably about 10 parts of an organic solvent, such as benzene, toluene, xylene or the like, at a temperature of from about 0° C. to about 100° C., and preferably at a temperature of about 25° C. to form a solution of the gallium trichloride; followed by the addition of 3 parts of sodium methoxide, preferably in a solution form, to provide a gallium methoxide solution, and a sodium chloride byproduct at a temperature of from about 0° C. to about 100° C., and preferably at a temperature of about 20° C. to about 40° C.; followed by the reaction with from about 1 part to about 10 parts, and preferably about 4 parts of ortho-phthalodinitrile or 1,3-diiminoisoindoline, and a diol, such as 1,2-ethanediol (ethylene glycol), 1,2-propanediol (propylene glycol) or 1,3-propanediol, in an amount of from about 3 parts to about 100 parts, and preferably about 10 parts for each part of the gallium methoxide formed, at a temperature of from about 150° C. to about 220° C., and preferably at a temperature of 195° C. for a period of 30 minutes to 6 hours, and preferably about 2 hours to provide an alkoxy-bridged gallium phthalocyanine dimer, which dimer pigment is isolated by filtration at a temperature of about 20° C. to about 180° C., and preferably at about 120° C. to give a dark blue solid identified by elemental analysis, infrared spectroscopy, proton NMR spectroscopy and XRD.

In another embodiment, the process of the present invention comprises the reaction of a metal trihalide, like gallium trichloride, with an alcohol, like methanol, ethanol or butanol, and a base such as ammonia, and subsequently reacting the resulting gallium alkoxide with, for example phthalodinitrile or 1,3-diiminoisoindoline, in the presence of a dialcohol (diol) which may also serve as a reaction solvent, to form the alkoxy-bridged gallium phthalocyanine dimers. Embodiments of the present invention are directed to the preparation of alkoxy-bridged gallium phthalocyanine dimers, which comprise the dissolution of 1 part of gallium trichloride in about 1 part to about 100 parts, and preferably about 10 parts of an organic solvent, such as benzene, toluene, xylene or the like, at a temperature of from about 0° C. to about 100° C., and preferably at a temperature of about 25° C. to form a solution of the gallium trichloride; followed by the addition of an alcohol, such as butanol, in about 1 part to about 10 parts, and preferably about 3 parts (by weight); followed by the addition of 3 parts of an amine, such as gaseous ammonia, at a temperature of from about 0° C. to about 60° C., and preferably at a temperature of about 25° C. to provide a gallium butoxide solution and an ammonium chloride byproduct; followed by a filtration step to remove the ammonium chloride; followed by reaction of the gallium butoxide solution with from about 1 part to about 10 parts, and preferably about 4 parts of orthophthalodinitrile or 1,3-diimiinoisoindoline, and a diol, such as 1,2-ethanediol (ethylene glycol), 1,2-propanediol (propylene glycol) or 1,3-propanediol, in an amount of from about 3 parts to about 100 parts, and preferably about 10 parts, for each part of the gallium butoxide formed at a temperature of from about 150° C. to about 220° C., and preferably at a temperature of 195° C. for a period of 30 minutes to 6 hours, and preferably about 2 hours to provide an alkoxy-bridged gallium phthalocyanine dimer, which dimer pigment is isolated by filtration at a temperature of about 20° C. to about 180° C., and preferably at about 120° C. to give a dark blue solid identified by elemental analysis, infrared spectroscopy, proton NMR spectroscopy and XRD.

Specific preferred embodiments of the present invention comprise initially preparing the trivalent metal alkoxide as indicated herein, which may then be separated from the byproduct or used in situ, followed by reaction of the metal alkoxide with phthalodinitrile or 1,3-diiminoisoindoline in a dialcohol (diol) solvent to form the alkoxy-bridged metallophthalocyanine dimer. During the aforementioned reaction, some of the dialcohol solvent is chemically incorporated into the dimer product as a bridging unit between the two metallophthalocyanine units. Embodiments of the present invention are directed to the preparation of alkoxy-bridged gallium phthalocyanine dimers, which comprise the dissolution of 1 part of gallium trichloride, in about 1 part to 100 parts, and preferably about 10 parts of an organic solvent such as benzene, toluene, xylene or the like, at a temperature of from about 0° C. to about 100° C., and preferably at a temperature of about 25° C. to form a solution of the gallium trichloride; followed by the addition of 3 parts of sodium methoxide, preferably in a solution form, to provide a gallium methoxide solution and a sodium chloride byproduct at a temperature of from about 0° C. to about 100° C., and preferably at a temperature of about 20° C. to about 40° C.; followed by the reaction with from about 1 part to about 10 parts, and preferably about 4 parts of orthophthalodinitrile or 1,3-diimiinoisoindoline, and 1,2-ethanediol (ethylene glycol) in an amount of from about 3 parts to about 100 parts, and preferably about 10 parts for each part of the gallium methoxide formed at a temperature of from about 150° C. to about 220° C., and preferably at a temperature of about 195° C. for a period of 30 minutes to 6 hours, and preferably about 2 hours to provide the alkoxy-bridged gallium phthalocyanine dimer 1,2-di(oxogallium phthalocyaninyl) ethane, $C_{32}H_{16}N_8GaOCH_2CH_2OGaN_8H_{16}C_{32}$, which dimer pigment is isolated by filtration at a temperature of about 20° C. to about 180° C., and preferably at about 120° C. to give a dark blue solid identified by elemental analysis, infrared spectroscopy, proton NMR spectroscopy and XRD.

The alkoxy-bridging unit includes components with from about 2 to about 12 and preferably from about 2 to about 6 carbon atoms, which are derived from the diol used in the phthalocyanine synthesis, such as 1,2-ethanediol, 1,2-propanediol, 1,3-propanediol, and the like.

The resulting alkoxy-bridged metallophthalocyanine dimers, such as alkoxy-bridged gallium phthalocyanine dimers, can be selected for utilization in layered photoconductive imaging members, including those that possess infrared photosensitivity, for example from about 600 to about 900 nanometers, and preferably from about 700 to about 850 nanometers, and wherein the dimer is selected as the photogenerating pigment. Alternatively, the alkoxy-bridged metallophthalocyanine dimer can be converted to the corresponding hydroxy metallophthalocyanine, which phthalocyanines may be selected as the photogenerating pigment.

In embodiments, the trivalent metal alkoxide can be obtained from the reaction of the corresponding metal trihalide with an alkali metal alkoxide, such as sodium methoxide, sodium ethoxide, sodium propoxide, sodium butoxide, the corresponding potassium alkoxides, and the like. The alkali metal halide byproduct formed can be separated from the reaction mixture by filtration, or the mixture may be utilized as is (in situ) in the subsequent reaction to form the alkoxy-bridged metallophthalocyanine dimers. In embodiments, the gallium alkoxide can be prepared by reacting a gallium trihalide, especially the trichloride and sodium methoxide, and, thereafter, reacting the resulting gallium methoxide with, for example, ortho-phthalodinitrile or 1,3-diiminoisoindoline in the presence of a dialcohol (diol), which may also serve as a reaction solvent, to form the alkoxy-bridged gallium phthalocyanine dimer.

Embodiments of the present invention are directed to processes for the preparation of alkoxy-bridged metallophthalocyanine dimers, which comprise the dissolution of 1 part of a trivalent metal halide, and preferably a metal trichloride in about 1 part to about 100 parts, and preferably about 10 parts of an organic solvent, such as benzene, toluene, xylene or the like, at a temperature of from about 0° C. to about 100° C., and preferably at a temperature of about 25° C. to form a solution of the metal trichloride; followed by the addition of 3 parts of an alkali metal alkoxide, such as sodium methoxide, sodium ethoxide, sodium propoxide or the like, preferably in a solution form to produce a trivalent metal alkoxide solution, and an alkali metal salt byproduct, for example sodium chloride, at a temperature of from about 0° C. to about 100° C., and preferably at a temperature of about 20° C. to about 40° C.; followed by the reaction with from about 1 part to about 10 parts, and preferably about 4 parts, of orthophthalodinitrile or 1,3-diiminoisoindolene, and a diol, including diols with from about 2 to about 12 carbon atoms, such as 1,2-ethanediol (ethylene glycol), 1,2-propanediol (propylene glycol) or 1,3-propanediol, in an amount of from about 3 parts to about 100 parts, and preferably about 10 parts, for each part of the metal alkoxide formed, at a temperature of from about 150° C. to about 220° C., and preferably at a temperature of 195° C. for a period of 30 minutes to 6 hours, and preferably about 2 hours to provide an alkoxy-bridged metallophthalocyanine dimer, which dimer pigment is isolated by, for example, filtration at a temperature of about 20° C. to about 180° C., and preferably at about 120° C. to provide a dark blue solid. Each dialcohol used for the phthalocyanine synthesis will provide a particular alkoxy-bridged metallophthalocyanine dimer product like, for example, 1,2-di(oxogallium phthalocyaninyl) ethane from 1,2-ethanediol. Similarly, using 1,3-propanediol for the phthalocyanine synthesis will provide an alkoxy-bridged metallophthalocyanine dimer like, for example, 1,3-di(oxogallium phthalocyaninyl) propane. The isolated pigment is subsequently washed with from about 1 part to about 20 parts of an organic solvent such as dimethylformamide, N-methylpyrrolidinone or dimethylsulfoxide, at a temperature of from about 20° C. to about 120° C., and preferably at a temperature of about 80° C. in order to remove reaction byproducts, followed by washing with aqueous solvents, such as aqueous ammonium hydroxide, aqueous sodium hydroxide, cold or hot water, to remove the alkali metal salt byproduct, and possibly another organic solvent wash, to provide a pure form of the alkoxy-bridged gallium phthalocyanine dimer, which has only a trace level of chlorine present. Each different diol used for the phthalocyanine synthesis will produce a particular alkoxy-bridged metallophthalocyanine dimer product, as determined by, for example, infrared (IR) spectroscopy, nuclear magnetic resonance (NMR) spectroscopy and X-ray powder diffraction pattern (XRD).

Embodiments of the present invention are directed to processes for the preparation of alkoxy-bridged gallium phthalocyanine dimers, which comprise the dissolution of 1 part of gallium trichloride, in about 1 part to about 100 parts, and preferably 10 parts of toluene at a temperature of from about 0° C. to about 100° C., and preferably at a temperature of about 25° C., to form a solution of gallium chloride; followed by the addition of 3 parts of an alkali metal alkoxide, and preferably a sodium alkoxide solution in methanol, to form a gallium alkoxide solution and sodium chloride byproduct, for example, at a temperature of from about 0° C. to about 100° C., and preferably at a temperature of about 20° C. to about 40° C.; followed by reaction with from about 1 part to about 10 parts, and preferably about 4 parts of orthophthalodinitrile, and 1,2-ethanediol (ethylene glycol) in an amount of from about 3 parts to about 100 parts, and preferably about 10 parts for each part of gallium alkoxide formed at a temperature of from about 150° C. to about 220° C., and preferably at a reflux temperature of about 190° C. to about 195°, for a period of 20 minutes to 6 hours, and preferably about 2 hours to provide the alkoxy-bridged gallium phthalocyanine dimer, 1,2-di(oxogallium phthalocyaninyl) ethane, $C_{32}H_{16}N_8GaOCH_2CH_2OGaN_8H_{16}C_{32}$, having an XRD pattern with major peaks at Bragg angles of 6.7, 8.9, 12.8, 13.9, 15.7, 16.6, 21.2, 25.3, 25.9 and 28.3, with the highest peak at 6.7 degrees 2Θ (2 theta +/−0.2°), which product is isolated by filtration at a temperature of about 20° C. to about 180° C., and preferably at about 120° C. to provide a dark blue solid. The isolated product pigment is subsequently washed with an organic solvent, such as dimethylformamide, in order to remove reaction byproducts at a temperature of from about 20° C. to about 120° C., and preferably at a temperature of about 80° C.; followed by optional washing with hot water in order to remove the alkali metal salt byproduct, and possibly another organic solvent like methanol to aid in subsequent drying of the product to provide a pure form, for example 98 to 99.9 percent of the alkoxy-bridged gallium phthalocyanine dimer in a yield of about 80 percent, calculated based upon the amount of gallium chloride used. The specific alkoxy-bridged gallium phthalocyanine dimer product resulting from the synthesis using ethylene glycol is 1,2-di(oxogallium phthalocyaninyl) ethane, $C_{32}H_{16}N_8GaOCH_2CH_2OGaN_8H_{16}C_{32}$, having an XRD pattern with major peaks at Bragg angles of 6.7, 8.9, 12.8, 13.9, 15.7, 16.6, 21.2, 25.3, 25.9 and 28.3, with the highest peak at 6.7 degrees 2Θ (2 theta +/−0.2°).

The processes of the present invention provide in embodiments high product yields, usually 75 to 85 percent, of the alkoxy-bridged gallium phthalocyanine dimer using raw materials readily available and process conditions which can readily be achieved in large scale operations, such as a 100 gallon scale. Furthermore, in embodiments, by first converting the gallium chloride to a gallium alkoxide, the processes provided herein yield alkoxy-bridged gallium phthalocyanine dimers which do not contain detrimental impurities, such as organic chlorinated derivatives, which can be observed when gallium chloride is used directly as the source of gallium in the synthesis of gallium phthalocyanines, which chlorine impurities result in higher levels of dark decay and cycledown when the phthalocyanine is used in photoreceptor applications.

One preferred alkoxy-bridged gallium phthalocyanine dimer obtained, 1,2-di(oxogallium phthalocyaninyl) ethane, $C_{32}H_{16}N_8GaOCH_2CH_2OGaN_8H_{16}C_{32}$, was characterized by elemental analysis, infrared spectroscopy, $^1$H NMR spectroscopy, $^{13}$C solid state CP/MAS NMR spectroscopy and X-ray powder diffraction. Elemental analysis provided values consistent with theory for the dimer structure, and in the preferred synthetic routes provided very low levels of residual chlorine, for example less than 0.11 percent, and, more specifically, from 0.01 to 0.10 percent. Infrared spectroscopy of 1,2-di(oxogallium phthalocyaninyl) ethane was performed by diffuse reflectance: major peaks at 573, 611, 636, 731,756, 775, 874, 897, 962, 999, 1069, 1088, 1125, 1165, 1289, 1337, 1424, 1466, 1503, 1611, 2569, 2607, 2648, 2864, 2950, and 3045 cm$^{-1}$ (FIG. 1). Infrared spectroscopy of the dimer does not show the characteristic broad hydroxyl group peak of hydroxygallium phthalocyanine at about 3,490 cm$^{-1}$, or the hydroxyl group peak expected for ethanediol (3,300 to 3,400 cm$^{-1}$). $^1$H NMR spectroscopy (in trifluoroacetic acid, TFA-d/CDCl$_3$ solution, 1:1 v/v, tetramethylsilane reference) (FIG. 2) has peaks at (δ, ppm±0.01 ppm) 4.00 (4H), 8.54 (16H), and 9.62 (16H). The relative integration of 4 protons being the two CH$_2$ units from the alkoxy-bridging unit (—OCH$_2$CH$_2$O—) between the two gallium phthalocyanine moieties, and the phthalocyanine dimer ring hydrogens appearing as two sets of 16 protons. The incorporated ethanediol (which forms the bridge) is liberated by hydrolysis during dissolution of the dimer in the TFA-d/CDCl$_3$ solvent. The $^{13}$C solid state CP/MAS (cross polarization/magic angle spinning) NMR spectrum has peaks at (δ, ppm±1 ppm) 60.8 (2CH$_2$), 124.0 (16CH), 129.1 (16CH), 135.5 (16C), and 152.6 (16C). All the NMR data are consistent with the formula $C_{32}H_{16}N_8GaOCH_2CH_2OGaN_8H_{16}C_{32}$ for 1,2-di(oxogallium phthalocyaninyl) ethane. The X-ray diffraction pattern has major peaks at Bragg angles of (2Θ±0.2°) 6.7, 8.9, 12.8, 13.9, 15.7, 16.6, 21.2, 25.3, 25.9 and 28.3, with the highest peak at 6.7 degrees 2Θ (FIG. 3).

A review of Examples I to XII illustrates that the processes described are useful for the synthesis of alkoxy-bridged metallophthalocyanine dimers. For example, by reacting gallium alkoxides, acetoacetonate, or acetate; or gallium alkoxides prepared from gallium trichloride as a process step in the phthalocyanine synthesis, with orthophthalodinitrile or 1,3-diiminoisoindoline, and a diol, an alkoxy-bridged gallium phthalocyanine dimer is obtained. The Comparative Examples 1 and 2 illustrate that when using gallium trichloride as the starting material, without converting it to an alkoxide, even in the presence of a diol, low yields, for example 16 to 45 percent of chlorogallium phthalocyanine, are obtained.

BRIEF DESCRIPTION OF THE FIGURES

For a better understanding of the present invention and further features thereof, reference is made to the following characterization data collected for the various preferred embodiments wherein.

The following Examples and Comparative Examples are provided. These examples are intended to be illustrative only. The invention is not intended to be limited to the materials, conditions, or process parameters recited herein. Percentages are by weight unless otherwise indicated.

EXAMPLE I

Figure 1:
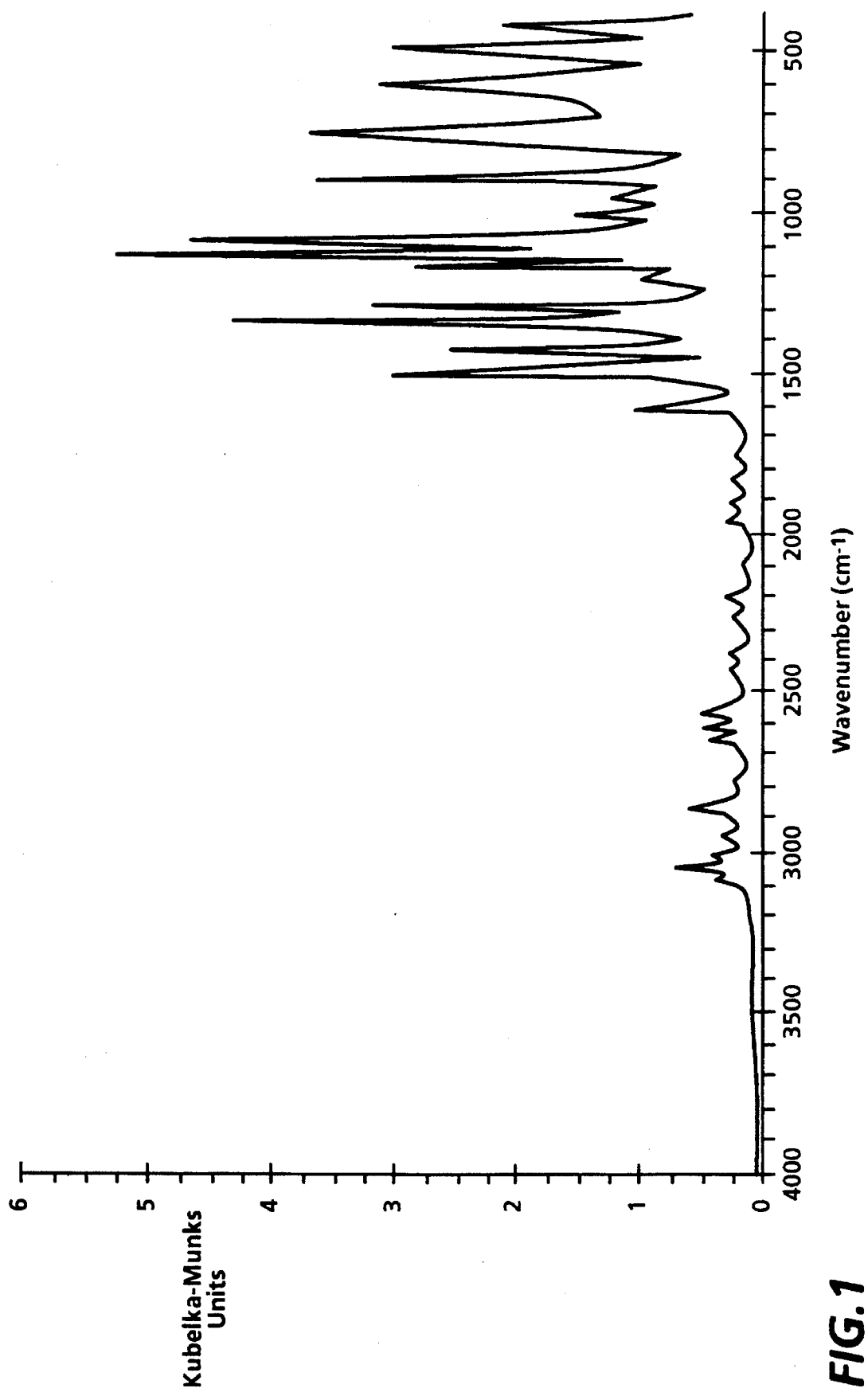
FIG. 1 represents a diffuse reflectance infrared plot of the alkoxy-bridged phthalocyanine dimer prepared as described in Example I, which has the formula $C_{32}H_{16}N_8GaOCH_2CH_2OGaN_8H_{16}C_{32}$.
Figure 2:
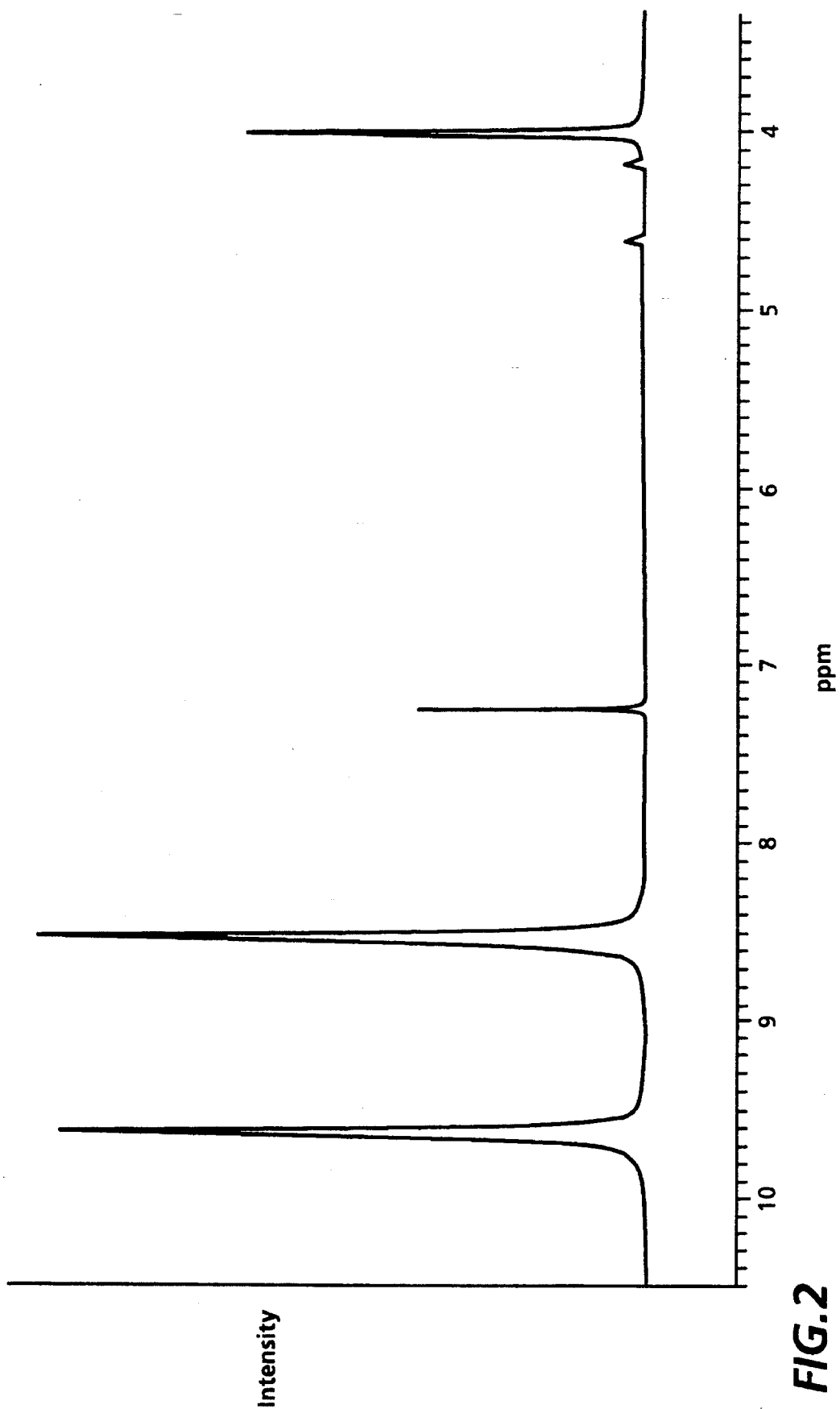
FIG. 2 represents a plot of $^1H$ NMR spectroscopy (in trifluoroacetic acid, TFA-d/CDCl$_3$ solution, 1:1 v/v, TMS reference) of the alkoxy-bridged phthalocyanine dimer prepared as described in Example I.
Figure 3:
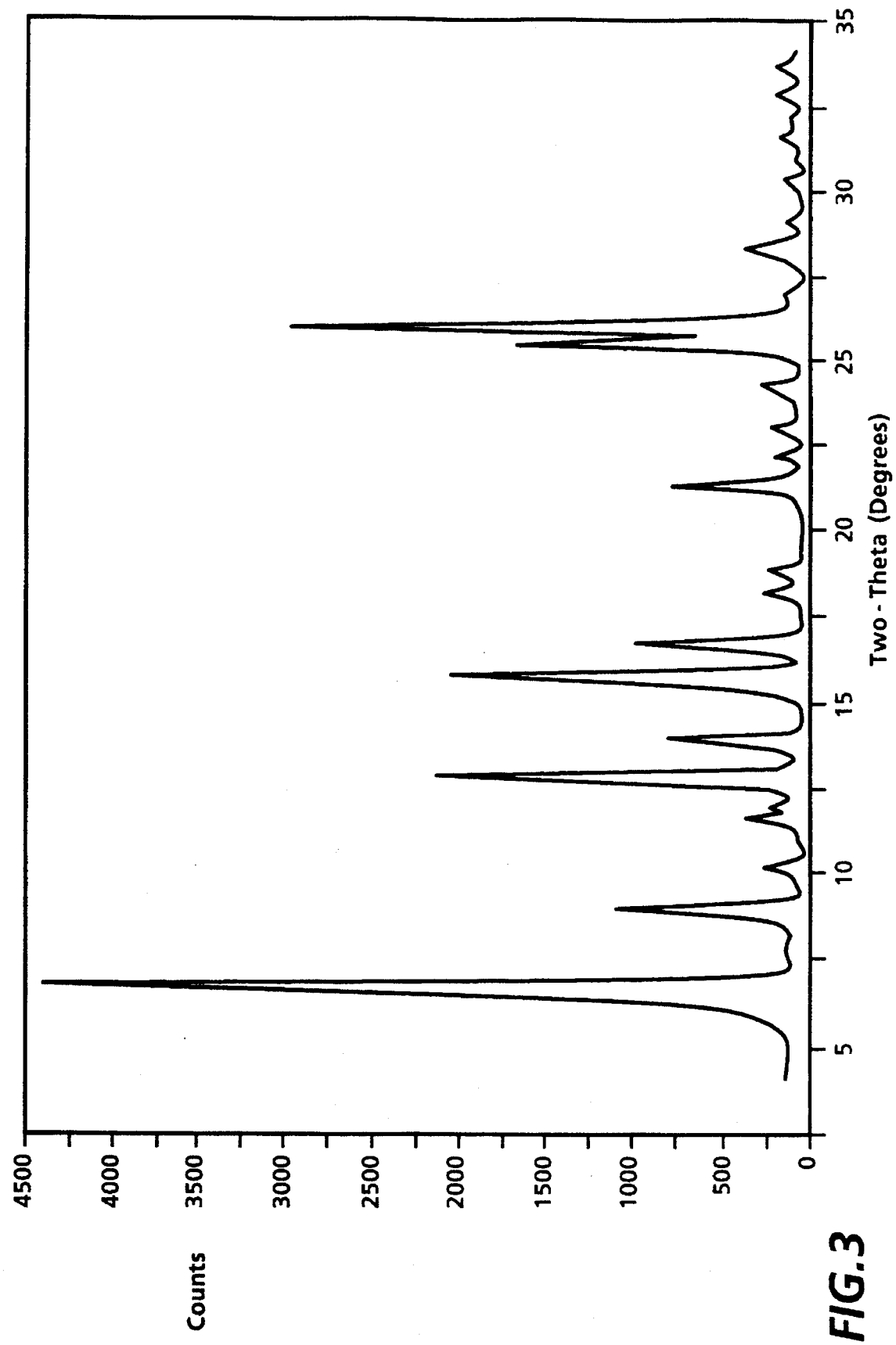
FIG. 3 represents an X-ray powder diffraction trace for the alkoxy-bridged gallium phthalocyanine dimer (Type I polymorph) prepared as described in Example I.

Alkoxy-bridged Gallium Phthalocyanine Dimer Synthesis Using Gallium Methoxide Obtained From Gallium Chloride and Sodium Methoxide In Situ:

To a 1 liter round bottomed flask were added 25 grams of GaCl$_3$ and 300 milliliters of toluene, and the mixture was stirred for 10 minutes to form a solution. Then, 98 milliliters of a 25 weight percent sodium methoxide solution (in methanol) was added while cooling the flask with an ice bath to keep the contents below 40° C. Subsequently, 250 milliliters of ethylene glycol and 72.8 grams of o-phthalodinitrile were added. The methanol and toluene were quickly distilled off in 30 minutes while heating from 70° C. to 135° C., and then the phthalocyanine synthesis was performed by heating at 195° C. for 2 hours. The alkoxy-bridged gallium phthalocyanine dimer was isolated by filtration at 120° C. The product was then washed with 400 milliliters of DMF at 100° C. for 1 hour and filtered. The product was then washed with 400 milliliters of deionized water at 80° C. for 1 hour and filtered. The product was then washed with 400 milliliters of methanol at 60° C. for 1 hour and filtered. The product was dried at 60° C. under vacuum for 18 hours. The alkoxy-bridged gallium phthalocyanine dimer product, 1,2-di(oxogallium phthalocyaninyl) ethane, was isolated as a dark blue solid in 80 percent yield. The dimer product was characterized by elemental analysis, infrared spectroscopy, $^1H$ NMR spectroscopy, $^{13}C$ solid state CP/MAS (cross polarization/magic angle spinning) NMR spectroscopy and X-ray powder diffraction. Elemental analysis showed the presence of 0.05 percent chlorine. Infrared spectroscopy: major peaks at 573, 611, 636, 731, 756, 775, 874, 897, 962, 999, 1069, 1088, 1125, 1165, 1289, 1337, 1424, 1466, 1503, 1611, 2569, 2607, 2648, 2864, 2950, and 3045 cm$^{-1}$ (FIG. 1); $^1H$ NMR spectroscopy (TFA-d/CDCl$_3$ solution, 1:1 v/v, tetramethylsilane reference): peaks at ($\delta$, ppm±0.01 ppm) 4.00 (4H), 8.54 (16H), and 9.62 (16H) (FIG. 2); $^{13}C$ solid state CP/MAS NMR spectroscopy: peaks at ($\delta$, ppm±1 ppm): 60.2 (2CH$_2$), 124.2 (16CH), 129.1 (16CH), 135.1 (16C), and 152.8 (16C); X-ray powder diffraction pattern: peaks at Bragg angles (2$\Theta$±0.2°) of 6.7, 8.9, 12.8, 13.9, 15.7, 16.6, 21.2, 25.3, 25.9, and 28.3, with the highest peak at 6.7 degrees 2$\Theta$ (FIG. 3).

EXAMPLE II

Alkoxy-bridged Gallium Phthalocyanine Dimer Synthesis Using Gallium Ethoxide Obtained From Gallium Chloride and Sodium Ethoxide In Situ:

To a 500 milliliter round bottomed flask were added 25 grams of GaCl$_3$ and 300 milliliters of toluene, and the resulting mixture was stirred for 10 minutes to form a solution. Then, 160 milliliters of a 21 weight percent sodium ethoxide solution (in ethanol) were added while cooling the flask with an ice bath to keep the contents below 60° C. The resulting mixture was stirred for 15 minutes and then filtered to remove the sodium chloride byproduct. The gallium ethoxide solution was then transferred to a 1 liter (1,000 milliliters) round bottomed flask, and 250 milliliters of ethylene glycol and 72.8 grams of o-phthalodinitrile were added. The ethanol and toluene were quickly distilled off in 30 minutes while heating from 90° C. to 135° C. The phthalocyanine synthesis was performed by heating the contents of the 1 liter flask at 195° C. for 4.5 hours. The alkoxy-bridged gallium phthalocyanine dimer was isolated by filtration at 120° C. The product was then washed with 400 milliliters of DMF (dimethylformamide) at 100° C. for 1 hour and filtered. The product was then washed with 400 milliliters of methanol at 60° C. for 1 hour and filtered. The product was dried at 60° C. under vacuum for 18 hours. The alkoxy-bridged gallium phthalocyanine dimer, 1,2-di(oxogallium phthalocyaninyl) ethane, was isolated as a dark blue solid in 62 percent yield. This product was characterized by elemental analysis, infrared spectroscopy, $^1H$ NMR spectroscopy and X-ray powder diffraction. Elemental analysis showed the presence of only 0.05 percent chlorine. Infrared spectroscopy: major peaks at 573, 611, 636, 731, 756, 775, 874, 897, 962, 999, 1069, 1088, 1125, 1165, 1289, 1337, 1424, 1466, 1503, 1611, 2569, 2607, 2648, 2864, 2950, and 3045 cm$^{-1}$ (identical to FIG. 1); $^1H$ NMR spectroscopy (TFA-d/CDCl$_3$ solution, 1:1 v/v, tetramethylsilane reference): peaks at ($\delta$, ppm±0.01 ppm) 4.00 (4H), 8.54 (16H), and 9.62 (16H) (identical to FIG. 2); X-ray powder diffraction pattern: peaks at Bragg angles (2$\Theta$±0.2°) of 6.7, 8.9, 12.8, 13.9, 15.7, 16.6, 21.2, 25.3, 25.9, and 28.3, with the highest peak at 6.7 degrees 2$\Theta$ (identical to FIG. 3).

EXAMPLE III

Alkoxy-bridged Gallium Phthalocyanine Dimer Synthesis Using Gallium Methoxide Obtained From Gallium Chloride and Sodium Methoxide In Situ:

To a 1 liter (1,000 milliliters) round bottomed flask were added 25 grams of GaCl$_3$ and 300 milliliters of toluene, and the mixture was stirred for 10 minutes to form a solution. Then, 98 milliliters of a 25 weight percent sodium methoxide solution (in methanol) were added while cooling the flask with an ice bath to keep the contents below 40° C. Subsequently, 250 milliliters of ethylene glycol and 72.8 grams of o-phthalodinitrile were added. The methanol and toluene were quickly distilled off in 30 minutes while heating from 70° C. to 135° C., and then the phthalocyanine synthesis was performed by heating at 195° C. for 4.5 hours. The alkoxy-bridged gallium phthalocyanine dimer was isolated by filtration at 120° C. The product was then washed with 400 milliliters of DMF at 100° C. for 1 hour and filtered. The product was then washed three times with 600 milliliters of an aqueous 10 percent NaOH solution at 25° C. for 0.5 hour, followed by several water washes, each with a filtration. The product was then washed with 600 milliliters of methanol at 25° C. for 1 hour and filtered. The product was dried at 60° C. under vacuum for 18 hours. The alkoxy-bridged gallium phthalocyanine dimer, 1,2-di(oxogallium phthalocyaninyl) ethane, was isolated as a dark blue solid in 77 percent yield. The dimer product was characterized by elemental analysis, infrared spectroscopy, $^1$H NMR spectroscopy and X-ray powder diffraction. Elemental analysis indicated the presence of only 0.10 percent chlorine. Infrared spectroscopy: major peaks at 573, 611, 636, 731, 756, 775, 874, 897, 962, 999, 1069, 1088, 1125, 1165, 1289, 1337, 1424, 1466, 1503, 1611, 2569, 2607, 2648, 2864, 2950, and 3045 cm$^{-1}$ (identical to FIG. 1); $^1$H NMR spectroscopy (TFA-d/CDCl$_3$ solution, 1:1 v/v, tetramethylsilane reference): peaks at ($\delta$, ppm±0.01 ppm) 4.00 (4H), 8.54 (16H), and 9.62 (16H) (identical to FIG. 2); X-ray powder diffraction pattern: peaks at Bragg angles (2$\Theta$±0.2°) of 6.7, 8.9, 12.8, 13.9, 15.7, 16.6, 21.2, 25.3, 25.9, and 28.3, with the highest peak at 6.7 degrees 2$\Theta$ (identical to FIG. 3).

EXAMPLE IV

Alkoxy-bridged Gallium Phthalocyanine Dimer Synthesis Using Gallium Ethoxide Obtained From Gallium Chloride and Sodium Ethoxide In Situ:

To a 1 liter round bottomed flask were added 250 milliliters of ethylene glycol and 25 grams of GaCl$_3$, and the mixture was stirred for 20 minutes to form a solution. Then, 160 milliliters of a 21 weight percent sodium ethoxide solution (in ethanol) were added while cooling the flask with an ice bath to keep the contents below 20° C. Thereafter, 72.8 grams of o-phthalodinitrile were added. The ethanol was quickly distilled off in 30 minutes while heating from 80° C. to 115° C., and then the phthalocyanine synthesis was performed by heating at 195° C. for 4 hours. The alkoxy-bridged gallium phthalocyanine dimer was isolated by filtration at 120° C. The product was then washed with 400 milliliters of DMF at 100° C. for 1 hour and filtered. The product was then washed with 400 milliliters of deionized water at 80° C. for 1 hour and filtered. The product was then washed with 400 milliliters of methanol at 60° C. for 1 hour and filtered. The product was dried at 60° C. under vacuum for 18 hours. The alkoxy-bridged gallium phthalocyanine dimer, 1,2-di(oxogallium phthalocyaninyl) ethane, was isolated as a dark blue solid in 62 percent yield. The dimer product was characterized by elemental analysis, infrared spectroscopy, $^1$H NMR spectroscopy and X-ray powder diffraction. Elemental analysis showed the presence of 0.23 percent chlorine. Infrared spectroscopy: major peaks at 573, 611, 636, 731, 756, 775, 874, 897, 962, 999, 1069, 1088, 1125, 1165, 1289, 1337, 1424, 1466, 1503, 1611, 2569, 2607, 2648, 2864, 2950, and 3045 cm$^{-1}$ (identical to FIG. 1); $^1$H NMR spectroscopy (TFA-d/CDCl$_3$ solution, 1:1 v/v, tetramethylsilane reference): peaks at ($\delta$, ppm±0.01 ppm) 4.00 (4H), 8.54 (16H), and 9.62 (16H) (identical to FIG. 2); X-ray powder diffraction pattern: peaks at Bragg angles (2$\Theta$±0.2°) of 6.7, 8.9, 12.8, 13.9, 15.7, 16.6, 21.2, 25.3, 25.9, and 28.3, with the highest peak at 6.7 degrees 2$\Theta$ (identical to FIG. 3).

EXAMPLE V

Alkoxy-bridged Gallium Phthalocyanine Dimer Synthesis Using Gallium Methoxide Obtained From Gallium Chloride and Sodium Methoxide In Situ:

To a 1 liter round bottomed flask were added 25 grams of GaCl$_3$ and 300 milliliters of toluene and the mixture was stirred for 10 minutes to form a solution. Then, 98 milliliters of a 25 weight percent sodium methoxide solution (in methanol) were added while cooling the flask with an ice bath to keep the contents below 40° C. Subsequently, 250 milliliters of ethylene glycol and 83.6 grams of 1,3-diiminoisoindoline were added. The methanol and toluene were quickly distilled off in 30 minutes while heating from 70° C. to 135° C., and then the phthalocyanine synthesis was performed by heating at 195° C. for 2 hours. The alkoxy-bridged gallium phthalocyanine dimer was isolated by filtration at 120° C. The product was then washed with 400 milliliters of DMF at 100° C. for 1 hour and filtered. The product was then washed with 400 milliliters of deionized water at 80° C. for 1 hour and filtered. The product was then washed with 400 milliliters of methanol at 60° C. for 1 hour and filtered. The product was dried at 60° C. under vacuum for 18 hours. The alkoxy-bridged gallium phthalocyanine dimer, 1,2-di(oxogallium phthalocyaninyl) ethane, was isolated as a dark blue solid in 75 percent yield. The product dimer photogenerating pigment was characterized by elemental analysis, infrared spectroscopy, $^1$H NMR spectroscopy and X-ray powder diffraction. Elemental analysis indicated the presence of 0.05 percent chlorine. Infrared spectroscopy: major peaks at 573, 611, 636, 731, 756, 775, 874, 897, 962, 999, 1069, 1088, 1125, 1165, 1289, 1337, 1424, 1466, 1503, 1611, 2569, 2607, 2648, 2864, 2950, and 3045 cm$^{-1}$ (identical to FIG. 1); $^1$H NMR spectroscopy (TFA-d/CDCl$_3$ solution, 1:1 v/v, tetramethylsilane reference): peaks at ($\delta$, ppm±0.01 ppm) 4.00 (4H), 8.54 (16H), and 9.62 (16H) (identical to FIG. 2); X-ray powder diffraction pattern: peaks at Bragg angles (2$\Theta$±0.2°) of 6.7, 8.9, 12.8, 13.9, 15.7, 16.6, 21.2, 25.3, 25.9, and 28.3, with the highest peak at 6.7 degrees 2$\Theta$ (identical to FIG. 3).

EXAMPLE VI

Alkoxy-bridged Gallium Phthalocyanine Dimer Synthesis Using Gallium Butoxide:

To a 1 liter round bottomed flask were added 41.1 grams of Ga(OBu)$_3$ purchased from All Chemie Ltd., Fort Lee, N.J., and 250 milliliters of ethylene glycol and 72.8 grams of o-phthalodinitrile. The butanol was distilled off over 30 minutes while heating from 120° C. to 150° C. and then the phthalocyanine synthesis was performed by heating at 195° C. for 4.5 hours. The alkoxy-bridged gallium phthalocyanine dimer was isolated by filtration at 120° C. The product was then washed with 400 milliliters of DMF at 100° C. for 1 hour and filtered. The product was then washed with 400 milliliters of methanol at 60° C. for 1 hour and filtered. The product was dried at 60° C. under vacuum for 18 hours. The alkoxy-bridged gallium phthalocyanine dimer, 1,2-di(oxogallium phthalocyaninyl) ethane, was isolated as a dark blue solid in 78 percent yield. The product dimer was characterized by elemental analysis, infrared spectroscopy and X-ray powder diffraction. Elemental analysis indicated the presence of only 0.02 percent chlorine. Infrared spectroscopy: major peaks at 573, 611, 636, 731, 756, 775, 874, 897, 962, 999, 1069, 1088, 1125, 1165, 1289, 1337, 1424, 1466, 1503, 1611, 2569, 2607, 2648, 2864, 2950, and 3045 cm$^{-1}$ (identical to FIG. 1); $^1$H NMR spectroscopy (TFA-d/CDCl$_3$ solution, 1:1 v/v, tetramethylsilane reference): peaks at ($\delta$, ppm±0.01 ppm) 4.00 (4H), 8.54 (16H), and 9.62 (16H) (identical to FIG. 2); X-ray powder diffraction pattern: peaks at Bragg angles (2$\Theta$±0.2°) of 6.7, 8.9, 12.8, 13.9, 15.7, 16.6, 21.2, 25.3, 25.9, and 28.3, with the highest peak at 6.7 degrees 2$\Theta$ (identical to FIG. 3).

EXAMPLE VII

Alkoxy-bridged Gallium Phthalocyanine Dimer Synthesis Using Gallium Acetylacetonate:

To a 1 liter round bottomed flask were added 53.4 grams of Ga(acac)$_3$ obtained from Varitech Custom Specialties, Deer Park, N.Y., and 250 milliliters of ethylene glycol and 74.6 grams of o-phthalodinitrile. The acetylacetonate (2,4-pentanedione) was distilled off over a period of 30 minutes and then the phthalocyanine synthesis was performed by heating at 195° C. for 2.5 hours. The alkoxy-bridged gallium phthalocyanine dimer was isolated by filtration at 120° C. The product was then washed with 400 milliliters of DMF at 100° C. for 1 hour and filtered. The product was then washed with 400 milliliters of methanol at 60° C. for 1 hour and filtered. The dark blue product was dried at 60° C. under vacuum for 18 hours. The alkoxy-bridged gallium phthalocyanine dimer, 1,2-di(oxogallium phthalocyaninyl) ethane, was isolated in 75 percent yield. The product dimer was characterized by elemental analysis, infrared spectroscopy, 1H NMR spectroscopy and X-ray powder diffraction. Elemental analysis indicated the presence of 0.02 percent chlorine. Infrared spectroscopy: major peaks at 573, 611, 636, 731, 756, 775, 874, 897, 962, 999, 1069, 1088, 1125, 1165, 1289, 1337, 1424, 1466, 1503, 1611, 2569, 2607, 2648, 2864, 2950, and 3045 cm$^{-1}$ (identical to FIG. 1); $^1$H NMR spectroscopy (TFAd/CDCl$_3$ solution, 1:1 v/v, tetramethylsilane reference): peaks at ($\delta$, ppm±0.01 ppm) 4.00 (4H), 8.54 (16H), and 9.62 (16H) (identical to FIG. 2); X-ray powder diffraction pattern: peaks at Bragg angles ($\Theta$±0.2°) of 6.7, 8.9, 12.8, 13.9, 15.7, 16.6, 21.2, 25.3, 25.9, and 28.3, with the highest peak at 6.7 degrees 2$\Theta$ (identical to FIG. 3).

EXAMPLE VIII

Alkoxy-bridged Gallium Phthalocyanine Dimer Synthesis Using Gallium Acetate:

To a 1 liter round bottomed flask were added 25.0 grams of Ga(OAc)$_3$ purchased from Advanced Materials, New Hill, N.C., and 190 milliliters of ethylene glycol and 51.9 grams of o-phthalodinitrile. The acetic acid was distilled off over a period of 30 minutes while heating from 115° C. to 150° C. and then the phthalocyanine synthesis was performed by heating at 195° C. for 5 hours. The alkoxy-bridged gallium phthalocyanine dimer was isolated by filtration at 120° C. The product was then washed with 400 milliliters of DMF at 100° C. for 1 hour and filtered. The product was then washed with 400 milliliters of methanol at 60° C. for 1 hour and filtered. The product was dried at 60° C. under vacuum for 18 hours. The alkoxy-bridged gallium phthalocyanine dimer, 1,2-di(oxogallium phthalocyaninyl) ethane, was isolated as a dark blue solid in 51 percent yield. The product dimer was characterized by elemental analysis, infrared spectroscopy, $^1$H NMR spectroscopy and X-ray powder diffraction. Elemental analysis showed the presence of 0.09 percent chlorine. Infrared spectroscopy: major peaks at 573, 611, 636, 731, 756, 775, 874, 897, 962, 999, 1069, 1088, 1125, 1165, 1289, 1337, 1424, 1466, 1503, 1611, 2569, 2607, 2648, 2864, 2950, and 3045 cm$^{-1}$ (identical to FIG. 1); $^1$H NMR spectroscopy (TFA-d/CDCl$_3$ solution, 1:1 v/v, tetramethylsilane reference): peaks at ($\delta$, ppm±0.01 ppm) 4.00 (4H), 8.54 (16H), and 9.62 (16H) (identical to FIG. 2); X-ray powder diffraction pattern: peaks at Bragg angles (2$\Theta$±0.2°) of 6.7, 8.9, 12.8, 13.9, 15.7, 16.6, 21.2, 25.3, 25.9, and 28.3, with the highest peak at 6.7 degrees 2$\Theta$ (identical to FIG. 3).

EXAMPLE IX

Large Scale Alkoxy-bridged Gallium Phthalocyanine Dimer Synthesis Using Gallium Methoxide Obtained From Gallium Chloride and Sodium Methoxide In Situ:

A 20 gallon glass-lined reactor was purged with nitrogen and charged with 32.0 kilograms of toluene. The reactor agitator was started and 3.00 kilograms gallium trichloride was loaded through the reactor loading port. The reactor loading port was closed, a nitrogen purge started, and the agitator speed increased to 200 rpm, while cooling was applied to the reactor jacket by a recirculating cooling system, and 11.04 kilograms of sodium methoxide solution (25 weight percent in methanol) was charged to the reactor from an addition vessel over a period of 30 minutes. The reactor was then charged with 8.73 kilograms of o-phthalodinitrile and 20 kilograms of ethylene glycol. The reactor was purged with nitrogen, after which heating was applied with a hot oil supply to the reactor jacket. During heating to a reaction temperature of 195° C. to 200° C., methanol and toluene were removed by distillation. After 20 kilograms of distillate have been removed, another 20 kilograms of ethylene glycol were charged in the reactor from an addition vessel over a period of 10 minutes. The reaction was carried out for 5 hours at 195° C. to 200° C. At the end of the 5 hour reaction period, cooling was applied using the recirculating cooling system. When the reactor temperature was 90° C., the reactor contents were discharged into an agitated vacuum filter and the filtrate drained. The crude material was reslurry washed in the agitated vacuum filter two times with 50 kilograms of DMF used to rinse the reactor. The washing was carried out two more times in the agitated vacuum filter with 100 kilograms of hot DMF at 75° C. to 90° C. The resulting material was then reslurry washed three times in the agitated vacuum filter with 50 kilograms of deionized water at 75° C. to 90° C. The wet cake resulting was then reslurry washed in the agitated vacuum filter three additional times for 30 minutes with 50 kilograms of warm methanol (45° C.) and filtered. The material was dried at 60° C. in a vacuum shelf dryer. 8.51 Kilograms of alkoxy-bridged gallium phthalocyanine dimer of Example VIII were obtained as a dark blue solid (81.4 percent yield). The dimer product obtained was characterized by elemental analysis, infrared spectroscopy, $^1$H NMR spectroscopy, $^{13}$C solid state CP/MAS (cross polarization/magic angle spinning) NMR spectroscopy and X-ray powder diffraction. Elemental analysis indicated the presence of only 0.09 percent chlorine. Infrared spectroscopy: major peaks at 573, 611, 636, 731, 756, 775, 874, 897, 962, 999, 1069, 1088, 1125, 1165, 1289, 1337, 1424, 1466, 1503, 1611, 2569, 2607, 2648, 2864, 2950, and 3045 cm$^{-1}$ (identical to FIG. 1); $^1$H NMR spectroscopy (TFA-d/CDCl$_3$ solution, 1:1 v/v, tetramethylsilane reference): peaks at ($\delta$, ppm±0.01 ppm) 4.00 (4H), 8.54 (16H), and 9.62 (16H) (identical to FIG. 2); $^{13}$C solid state CP/MAS NMR spectroscopy: peaks at ($\delta$, ppm±1 ppm): 60.5 (2CH$_2$), 123.4 (16CH), 128.5 (16CH), 135.0 (16C), and 152.4 (16C); X-ray powder diffraction pattern: peaks at Bragg angles (2Θ±0.2°) of 6.7, 8.9, 12.8, 13.9, 15.7, 16.6, 21.2, 25.3, 25.9, and 28.3, with the highest peak at 6.7 degrees 2Θ (identical to FIG. 3).

EXAMPLE X

Alkoxy-bridged Gallium Phthalocyanine Dimer Synthesis Using Gallium Butoxide Obtained From Gallium Chloride and Butanol With Ammonia Ex Situ:

To a 500 milliliter round bottomed flask were added 25 grams of GaCl$_3$ and 200 milliliters of toluene, and the mixture was stirred for 10 minutes to form a solution. Then, 70 milliliters of n-butanol were added, followed by 7.7 grams of ammonia bubbled into the solution while cooling the flask with an ice bath to keep the contents below 30° C. The mixture was stirred for 15 minutes and then transferred to a vacuum filter and filtered to remove the ammonium chloride byproduct. The filtercake was rinsed with 100 milliliters of toluene and then the gallium butoxide filtrate solution was transferred to a 1 liter round bottomed flask. Thereafter, 250 milliliters of ethylene glycol and 72.8 grams of o-phthalodinitrile were added. The butanol and toluene were quickly distilled off over 30 minutes while heating from 110° C. to 135° C., and then the phthalocyanine synthesis was performed by heating at 195° C. for 4.5 hours. The alkoxy-bridged gallium phthalocyanine dimer product was isolated by filtration at 120° C. The product was then washed with 400 milliliters of DMF at 100° C. for 1 hour and filtered. The product was then washed with 400 milliliters of methanol at 60° C. for 1 hour and filtered. The product was dried at 60° C. under vacuum for 18 hours. The alkoxy-bridged gallium phthalocyanine dimer, 1,2-di(oxogallium phthalocyaninyl) ethane, was isolated as a dark blue solid in 40 percent yield. The pigment was characterized by elemental analysis, infrared spectroscopy, $^1$H NMR spectroscopy and X-ray powder diffraction. Elemental analysis showed the presence of 0.51 percent chlorine. Infrared spectroscopy: major peaks at 573, 611, 636, 731, 756, 775, 874, 897, 962, 999, 1069, 1088, 1125, 1165, 1289, 1337, 1424, 1466, 1503, 1611, 2569, 2607, 2648, 2864, 2950, and 3045 cm$^{-1}$ (identical to FIG. 1); $^1$H NMR spectroscopy (TFA-d/CDCl$_3$ solution, 1:1 v/v, tetramethylsilane reference): peaks at ($\delta$, ppm±0.01 ppm) 4.00 (4H), 8.54 (16H), and 9.62 (16H) (identical to FIG. 2); X-ray powder diffraction pattern: peaks at Bragg angles (2Θ±0.2°) of 6.7, 8.9, 12.8, 13.9, 15.7, 16.6, 21.2, 25.3, 25.9, and 28.3, with the highest peak at 6.7 degrees 2Θ (identical to FIG. 3).

EXAMPLE XI

Figure 4:
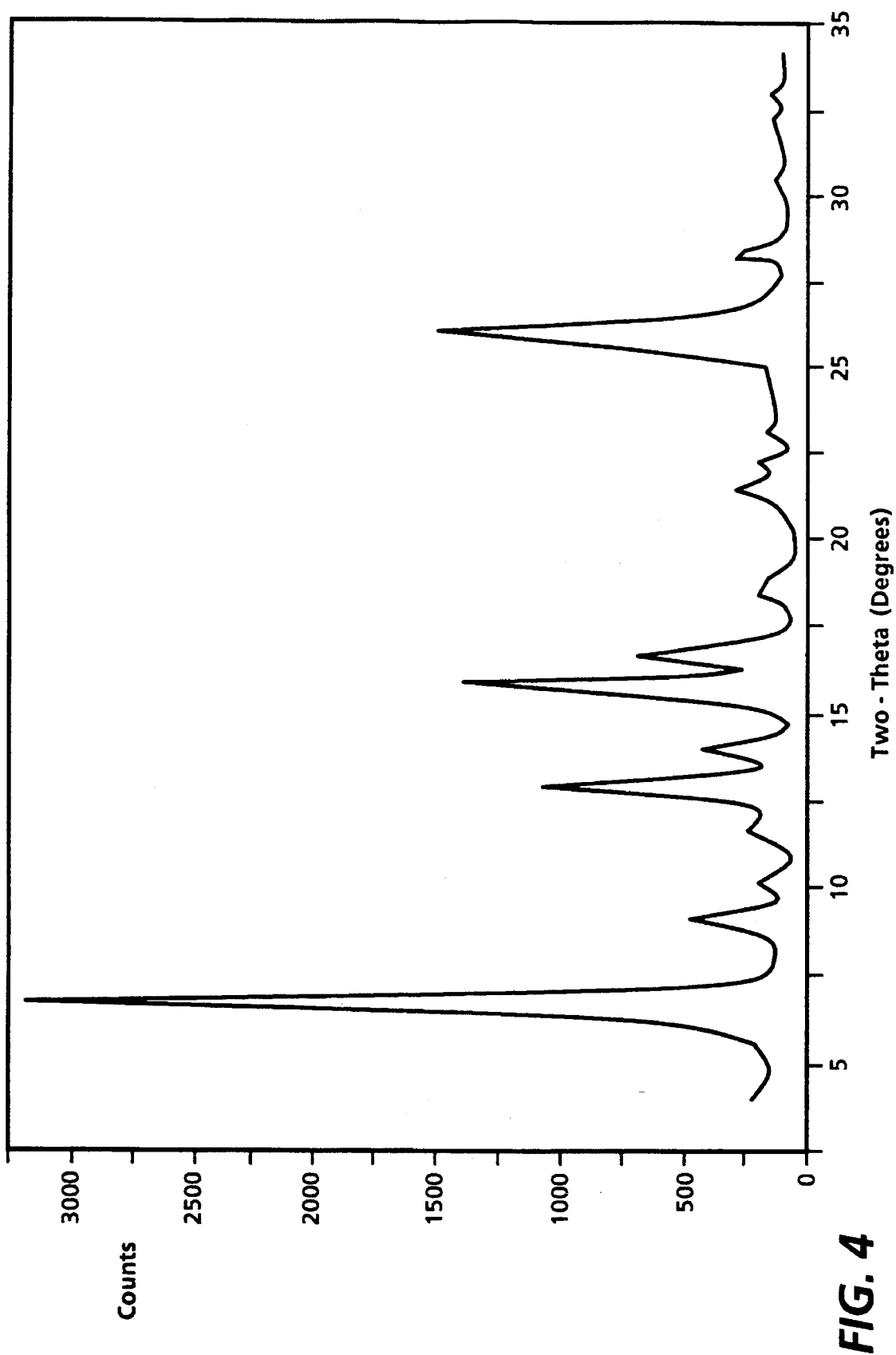
FIG. 4 represents an X-ray powder diffraction trace for the alkoxy-bridged gallium phthalocyanine dimer (Type I polymorph with a lower level of crystal orientation) prepared as described in Example IX.

Synthesis of Alkoxy-bridged Gallium Phthalocyanine Dimer From Hydroxygallium Phthalocyanine at 120° C.:

To a 500 milliliter round bottomed flask were added 6.0 grams of hydroxygallium phthalocyanine and 200 milliliters of ethylene glycol. The mixture was stirred while heating at 120° C. for 5 hours. The alkoxy-bridged gallium phthalocyanine dimer was isolated by filtration and then twice washed with 200 milliliters of methanol. The product was dried at 60° C. under vacuum for 18 hours. The alkoxy-bridged gallium phthalocyanine dimer, 1,2-di(oxogallium phthalocyaninyl) ethane, was isolated as a dark blue solid in 90 percent yield. The dimer product pigment was characterized by infrared spectroscopy, $^1$H NMR spectroscopy and X-ray powder diffraction. Infrared spectroscopy: major peaks at 573, 611, 636, 731, 756, 775, 874, 897, 962, 999, 1069, 1088, 1125, 1165, 1289, 1337, 1424, 1466, 1503, 1611, 2569, 2607, 2648, 2864, 2950, and 3045 cm$^{-1}$ (identical to FIG. 1); $^1$H NMR spectroscopy (TFA-d/CDCl$_3$ solution, 1:1 v/v, tetramethylsilane reference): peaks at ($\delta$, ppm±0.01 ppm) 4.00 (4H), 8.54 (16H), and 9.62 (16H) (identical to FIG. 2); X-ray powder diffraction pattern: peaks at Bragg angles (2Θ±0.2°) of 6.7, 8.9, 12.8, 13.9, 15.7, 16.6, 25.9, and 28.3, with the highest peak at 6.7 degrees 2Θ (FIG. 4).

EXAMPLE XII

Synthesis of Alkoxy-bridged Gallium Phthalocyanine Dimer From Hydroxygallium Phthalocyanine at 190° C.:

To a 500 milliliter round bottomed flask were added 6.0 grams of hydroxygallium phthalocyanine and 200 milliliters of ethylene glycol. The mixture was stirred while heating at 190° C. for 5 hours. The alkoxy-bridged gallium phthalocyanine dimer was isolated by filtration and then twice washed with 200 milliliters of methanol. The product was dried at 60° C. under vacuum for 18 hours. The alkoxy-bridged gallium phthalocyanine dimer, 1,2-di(oxogallium phthalocyaninyl) ethane, was isolated as a dark blue solid in 90 percent yield. The dimer product pigment was characterized by infrared spectroscopy, $^1$H NMR spectroscopy, $^{13}$C solid state CP/MAS (cross polarization/magic angle spinning) NMR spectroscopy and X-ray powder diffraction. Infrared spectroscopy: major peaks at 573, 611, 636, 731, 756, 775, 874, 897, 962, 999, 1069, 1088, 1125, 1165, 1289, 1337, 1424, 1466, 1503, 1611, 2569, 2607, 2648, 2864, 2950, and 3045 cm$^{-1}$ (identical to FIG. 1); $^1$H NMR spectroscopy (TFA-d/CDCl$_3$ solution, 1:1 v/v, tetramethylsilane reference): peaks at ($\delta$, ppm±0.01 ppm) 4.00 (4H), 8.54 (16H), and 9.62 (16H) (identical to FIG. 2); $^{13}$C solid state CP/MAS NMR spectroscopy: peaks at ($\delta$, ppm±1 ppm): 60.2 (2CH$_2$), 124.2 (16CH), 129.1 (16CH), 135.1 (16C), 152.8 (16C); X-ray powder diffraction pattern: peaks at Bragg angles (2Θ±0.2°) of 6.7, 8.9, 12.8, 13.9, 15.7, 16.6, 21.2, 25.3, 25.9, and 28.3, with the highest peak at 6.7 degrees 2Θ (identical to FIG. 3).

COMPARATIVE EXAMPLE 1

Figure 5:
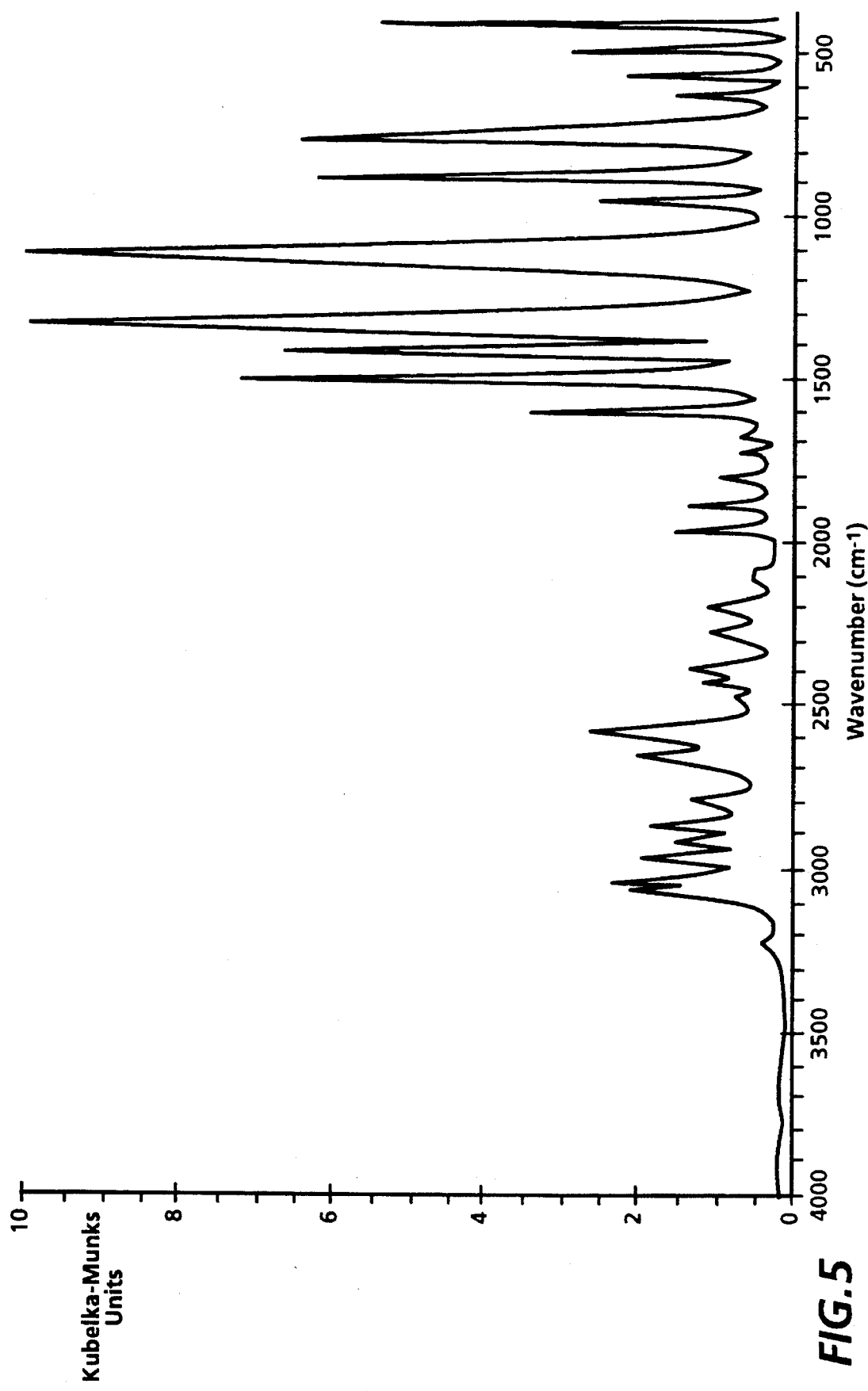
FIG. 5 represents an infrared plot of chlorogallium phthalocyanine prepared as described in Comparative Example 1.
Figure 6:
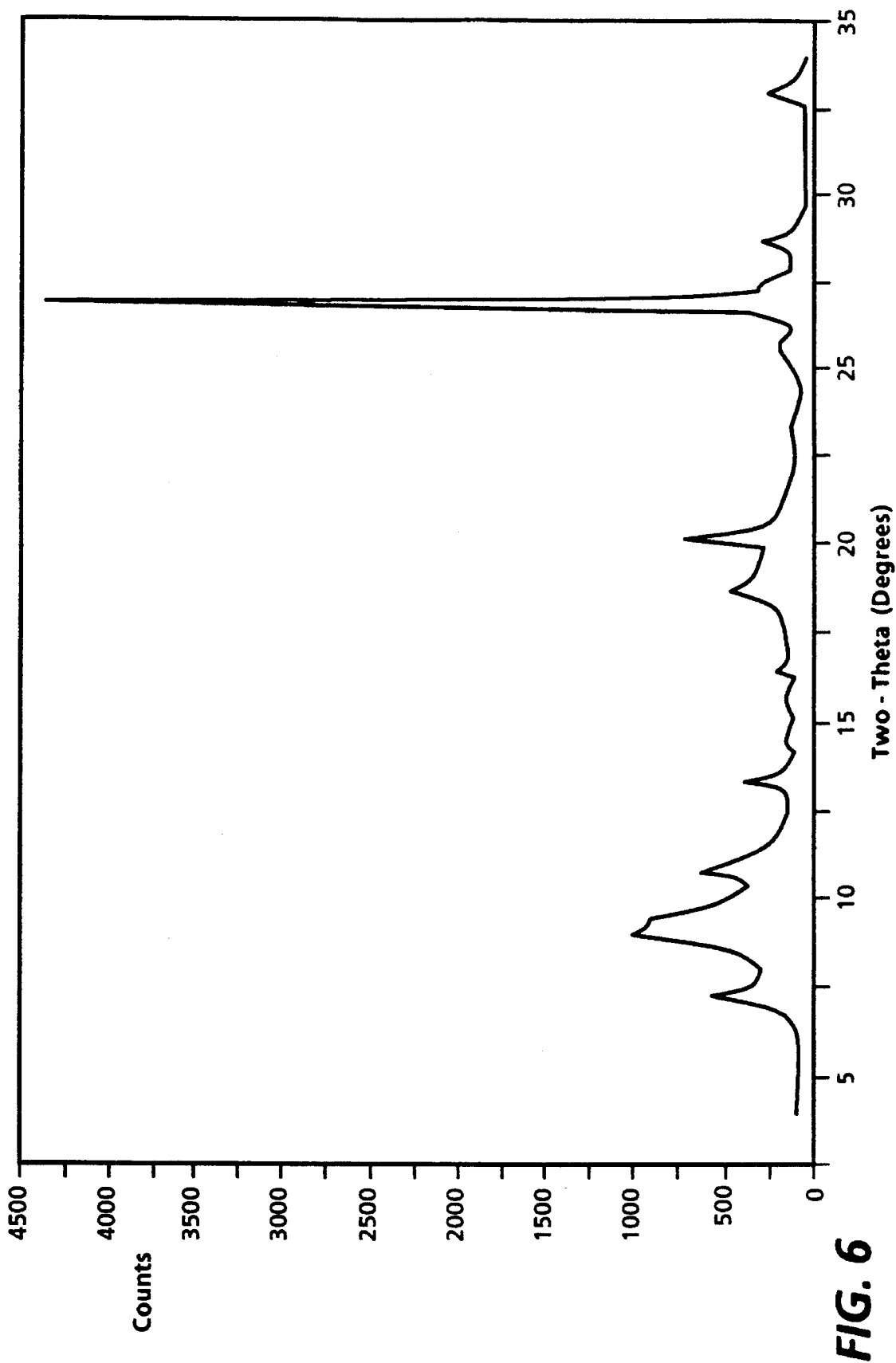
FIG. 6 represents an X-ray powder diffraction trace for chlorogallium phthalocyanine (Type I polymorph) prepared as described in Comparative Example 1.

Chlorogallium Phthalocyanine Synthesis From Gallium Chloride in Ethylene Glycol, Without the Use of an Alkali Metal Alkoxide to Form a Gallium Alkoxide:

To a 1 liter round bottomed flask were added 25 grams of GaCl$_3$ and 200 milliliters of toluene, and the mixture was stirred for 10 minutes to form a solution. Then, 250 milliliters of ethylene glycol and 82.5 grams of 1,3-diiminoisoindoline were added. The toluene was distilled off over 30 minutes while heating from 110° to 135° C., and then the phthalocyanine synthesis was performed by heating at 195° C. for 4 hours. The chlorogallium phthalocyanine was isolated by filtration at 120° C. The product was then washed with 400 milliliters of DMF at 100° C. for 1 hour and filtered. The product was then washed with 400 milliliters of methanol at 60° C. for 1 hour and filtered. The product was dried at 60° C. under vacuum for 18 hours. The chlorogallium phthalocyanine (Type I) was isolated as a dark blue solid in 45 percent yield, and no dimer was obtained. The product pigment was characterized by elemental analysis, infrared spectroscopy and X-ray powder diffraction. Elemental analysis showed the presence of 6.1 percent chlorine (theoretical-value for ClGaPc is 5.74 percent). Infrared spectroscopy: major peaks at 432, 507, 573, 638, 718, 754, 779, 866, 897, 947, 995, 1067, 1088, 1125, 1169, 1288, 1339, 1424, 1468, 1484, 1507, 1589, 1607, 1638, 1680, 1732, 1810, 1848, 1891, 1929, 1967, 2197, 2237, 2269, 2388, 2426, 2577, 2612, 2652, 2783, 2824, 2861, 2914, 2857, 3013, 3030, 3053 and 3084 $cm^{-1}$ (FIG. 5); X-ray diffraction pattern: peaks at Bragg angles of 7.3, 9.1, 10.9, 13.4, 18.6, 20.3, 27.0, 28.8 and 33.1, with the highest peak at 27.0 degrees 2Θ (2 theta +/–0.2°) (FIG. 6).

COMPARATIVE EXAMPLE 2

Chlorogallium Phthalocyanine Synthesis From Gallium Chloride and Ammonia in Ethylene Glycol, Without Forming a Gallium Alkoxide:

To a 1 liter round bottomed flask were added 25 grams of $GaCl_3$ and 250 milliliters of ethylene glycol, and the mixture was stirred for 20 minutes to form a solution. Then, 7.3 grams of ammonia were bubbled into the solution while cooling the flask with an ice bath to keep the contents below 45° C. Then, 72.8 grams of o-phthalodinitrile were added and the phthalocyanine synthesis was performed by heating at 195° C. for 4.5 hours. The chlorogallium phthalocyanine was isolated by filtration at 120° C. The product was then washed with 400 milliliters of DMF at 100° C. for 1 hour and filtered. The product was then washed with 400 milliliters of deionized water at 90° C. for 1.5 hours and filtered. The product was then washed with 400 milliliters of methanol at 30° C. for 15 minutes and filtered. The product was dried at 60° C. under vacuum for 18 hours. The chlorogallium phthalocyanine Type I pigment was isolated as a dark blue solid in 16 percent yield, and no dimer was obtained. The pigment was characterized by elemental analysis, infrared spectroscopy and X-ray powder diffraction. Elemental analysis showed the presence of 6.1 percent chlorine (theoretical value for ClGaPc is 5.74 percent). Elemental analysis showed the presence of 5.04 percent chlorine. Infrared spectroscopy: major peaks at 432, 507, 573, 638, 718, 754, 779, 866, 897, 947, 995, 1067, 1088, 1125, 1169, 1288, 1339, 1424, 1468, 1484, 1507, 1589, 1607, 1638, 1680, 1732, 1810, 1848, 1891, 1929, 1967, 2197, 2237, 2269, 2388, 2426, 2577, 2612, 2652, 2783, 2824, 2861, 2914, 2857, 3013, 3030, 3053 and 3084 $cm^{-1}$ (identical to FIG. 5); X-ray diffraction pattern: peaks at Bragg angles of 7.3, 9.1, 10.9, 13.4, 18.6, 20.3, 27.0, 28.8 and 33.1, with the highest peak at 27.0 degrees 2Θ (2 theta +/–0.2°) (identical to FIG. 6).

COMPARATIVE EXAMPLE 3

Chlorogallium Phthalocyanine Synthesis Using Gallium Trichloride in 1-Chloronaphthalene:

To a 5 liter round bottomed flask equipped with stirring and a nitrogen purge atmosphere were added 200 grams of $GaCl_3$ plus 582 grams of o-phthalodinitrile and 2.75 liters of 1-chloronaphthalene. The phthalocyanine synthesis was performed by heating at 200° C. for 4 hours. The phthalocyanine was filtered at 120° C. and then washed in the filter with 350 milliliters of DMF. The product was then washed in a beaker with 1.5 liter of DMF at 22° C. for 30 minutes and filtered. The product was then washed in a beaker with 1.5 liters of DMF at 100° C. for 1 hour and filtered. The product was then washed again at 22° C. for 30 minutes in a beaker with 1.5 liters of DMF and filtered. The product was then washed in a beaker with 1.5 liters of methanol at 65° C. for 1 hour and filtered. The product was then washed again at 22° C. for 30 minutes in a beaker with 1.5 liters of methanol and filtered. The wet cake resulting was dried at 60° C. under vacuum for 18 hours resulting in 271 grams of dark blue chlorogallium phthalocyanine Type T pigment, 39 percent yield, and no dimer was obtained. The pigment was characterized by elemental analysis, infrared spectroscopy and X-ray powder diffraction. Elemental analysis showed the presence of 5.60 percent chlorine (theoretical value for ClGaPc is 5.74 percent). Infrared spectroscopy: major peaks at 432, 507, 573, 638, 718, 754, 779, 866, 897, 947, 995, 1067, 1088, 1125, 1169, 1288, 1339, 1424, 1468, 1484, 1507, 1589, 1607, 1638, 1680, 1732, 1810, 1848, 1891, 1929, 1967, 2197, 2237, 2269, 2388, 2426, 2577, 2612, 2652, 2783, 2824, 2861, 2914, 2857, 3013, 3030, 3053 and 3084 $cm^{-1}$ (identical to FIG. 5); X-ray diffraction pattern: peaks at Bragg angles of 7.3, 9.1, 10.9, 13.4, 18.6, 20.3, 27.0, 28.8 and 33.1, with the highest peak at 27.0 degrees 2Θ (2 theta +/–0.2°) (identical to FIG. 6).

Other embodiments and modifications of the present invention may occur to those skilled in the art subsequent to a review of the information presented herein; these embodiments and modifications, as well as equivalents thereof, are also included within the scope of this invention.

What is claimed is:

1. A process for the preparation of alkoxy-bridged metallophthalocyanine dimers by the reaction of a gallium alkoxide with ortho-phthalodinitrile or 1,3-diiminoisoindoline in the presence of a diol.

2. A process in accordance with claim 1 wherein the metallophthalocyanine dimers are of the formula $C_{32}H_{16}N_8MOROMN_8H_{16}C_{32}$ wherein M is gallium and R is an alkyl group or an alkyl ether

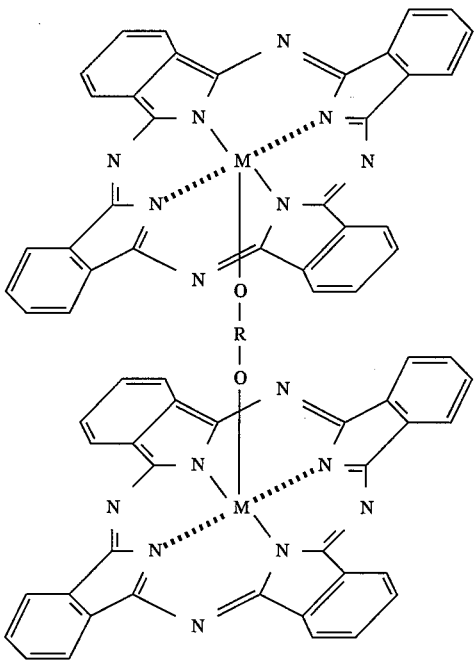

3. A process in accordance with claim 1 wherein the phthalocyanine dimer is of the formula $C_{32}H_{16}N_8GaOROGaN_8H_{16}C_{32}$ wherein R is alkyl.

4. A process in accordance with claim 1 wherein the diol is an alkane diol with from 2 to about 12 carbon atoms.

5. A process in accordance with claim 4 wherein the diol is 1,3-propanediol, 2-methyl-1,3-propanediol, 2,2-dimethyl-1,3-propanediol, 1,3-butanediol, 1,4-butanediol, 3-methyl-1,4-butanediol or 1,6-hexanediol.

6. A process in accordance with claim 1 wherein the diol is a 1,2-alkanediol with from 2 to about 12 carbon atoms.

7. A process in accordance with claim 6 wherein the diol is 1,2-ethanediol (ethylene glycol), 1,2-propanediol (propylene glycol) or 1,2-butanediol (butylene glycol).

8. A process in accordance with claim 1 wherein the diol is an ether with from 4 to about 12 carbon atom.

9. A process in accordance with claim 8 wherein the diol is diethylene glycol, triethylene glycol, or dipropylene glycol.

10. A process in accordance with claim 1 wherein the diol is ethylene glycol or propylene glycol.

11. A process in accordance with claim 1 wherein the phthalocyanine dimer product is $C_{32}H_{16}N_8GaOCH_2CH_2OGaN_8H_{16}C_{32}$, 1,2-di(oxogallium phthalocyaninyl) ethane; $C_{32}H_{16}N_8GaOCH(CH_3)CH_2OGaN_8H_{16}C_{32}$, 1,2-di(oxogallium phthalocyaninyl) propane; $C_{32}H_{16}N_8GaOCH_2CH_2CH_2OGaN_8H_{16}C_{32}$, 1,3-di(oxogallium phthalocyaninyl) propane; or $C_{32}H_{16}N_8GaOCH_2CH_2CH_2CH_2OGaN_8H_{16}C_{32}$, 1,4-di(oxogallium phthalocyaninyl) butane.

12. A process in accordance with claim 1 wherein the gallium alkoxide contains from 3 to about 24 carbon atoms.

13. A process in accordance with claim 1 wherein the alkoxide is methoxide, ethoxide, propoxide, butoxide, pentoxide or 2-ethylhexoxide.

14. A process in accordance with claim 1 wherein the trivalent metal alkoxide is a gallium methoxide.

15. A process in accordance with claim 1 wherein the gallium alkoxide is obtained from the reaction of the corresponding gallium trihalide with an alkali metal alkoxide in a solvent, followed by removing the alkali metal halide byproduct, and selecting the trivalent gallium alkoxide solution for the reaction with ortho-phthalodinitrile or 1,3-diiminoisoindoline, and a diol to form the alkoxy-bridged metallophthalocyanine dimer.

16. A process in accordance with claim 1 wherein the gallium alkoxide is obtained from the reaction of the corresponding gallium trihalide with an alkali metal alkoxide in a solvent, and selecting a mixture of gallium alkoxide and alkali metal halide byproduct in a solvent for the reaction with ortho-phthalodinitrile or 1,3-diiminoisoindoline, and a diol to form the alkoxy-bridged metallophthalocyanine dimer.

17. A process in accordance with claim 16 wherein the solvent is an organic halogenated solvent or an organic nonhalogenated solvent.

18. A process in accordance with claim 16 wherein the solvent is an aromatic solvent.

19. A process in accordance with claim 18 wherein the solvent is benzene, toluene, or xylene.

20. A process in accordance with claim 1 wherein the gallium alkoxide is obtained from the reaction of the corresponding metal trihalide in a solvent with an alcohol in the presence of a base, followed by removing the base halide byproduct, and selecting the gallium alkoxide solution for the reaction with ortho-phthalodinitrile or 1,3-diiminoisoindoline, and a diol to form the alkoxy-bridged metallophthalocyanine dimer.

21. A process in accordance with claim 20 wherein the solvent is an organic halogenated or an organic nonhalogenated solvent.

22. A process in accordance with claim 20 wherein the solvent is an organic solvent in which the formed trivalent metal alkoxide is soluble.

23. A process in accordance with claim 20 wherein the solvent is the aromatic solvent benzene, toluene, or xylene.

24. A process in accordance with claim 1 wherein the gallium alkoxide is obtained from the reaction of the corresponding metal trihalide with an alkali gallium alkoxide in a solvent, and selecting the mixture of trivalent gallium alkoxide and alkali metal halide byproduct for the reaction with orthophthalodinitrile or 1,3-diiminoisoindoline, and a diol with an additional reaction solvent, to form the alkoxy-bridged metallophthalocyanine dimer.

25. A process for the preparation of alkoxy-bridged metallophthalocyanine dimers consisting essentially of the dissolution of 1 part of a trivalent metal halide in about 1 part to about 100 parts of the organic solvent benzene, toluene, or xylene, at a temperature of from about 0° C. to about 100° C. to form a solution of the metal trichloride; followed by the addition of 3 parts of the alkali metal alkoxide, sodium methoxide, sodium ethoxide, or sodium propoxide to provide a trivalent metal alkoxide solution, and an alkali metal salt byproduct of sodium chloride, at a temperature of from about 0° C. to about 100° C.; followed by the reaction thereof with from about 1 part to about 10 parts of ortho-phthalodinitrile or 1,3-diiminoisoindoline, and a diol of 1,2-ethanediol (ethylene glycol), 1,2-propanediol (propylene glycol) or 1,3-propanediol in an amount of from about 3 parts to about 100 parts for each part of the metal alkoxide formed, at a temperature of from about 150° C. to about 220° C. for a period of 30 minutes to 6 hours to provide an alkoxy-bridged metallophthalocyanine dimer, which dimer is isolated by filtration at a temperature of about 20° C. to about 180° C.

26. A process in accordance with claim 1 for the preparation of alkoxy-bridged metallophthalocyanine dimers, which comprises the dissolution of 1 part of a trivalent metal halide in about 1 part to about 100 parts of an organic solvent at a temperature of from about 0° C. to about 100° C. to form a solution of the metal trichloride; followed by the addition of 3 parts of an alkali metal alkoxide to provide a trivalent metal alkoxide solution, and an alkali metal salt byproduct at a temperature of from about 0° C. to about 100° C.; followed by the reaction thereof with from about 1 part to about 10 parts of ortho-phthalodinitrile or 1,3-diiminoisoindoline, and a diol in an amount of from about 3 parts to about 100 parts for each part of the metal alkoxide formed at a temperature of from about 150° C. to about 220° C. to provide an alkoxy-bridged metallophthalocyanine dimer, which dimer is isolated by filtration at a temperature of about 20° C. to about 180° C.; followed by optional washing of said dimer product with an organic solvent at a temperature of from about 20° C. to about 120° C.; followed by optional washing with an aqueous solvent, or water to provide a pure form of the alkoxy-bridged metallophthalocyanine dimer.

27. A process in accordance with claim 25 wherein said trivalent metal halide is a metal trichloride, said dissolution is accomplished at a temperature of about 25° C., and the trivalent metal alkoxide solution and alkali metal salt are obtained at a temperature of about 20° C. to about 40° C.

28. An in situ process for the preparation of alkoxy-bridged metallophthalocyanine dimers consisting essentially of the reaction of a metal halide and an alkali metal alkoxide to form in situ a metal alkoxide, and thereafter reacting said metal alkoxide with ortho-phthalodinitrile in the presence of a diol.

29. A process in accordance with claim 28 wherein there is formed an alkoxy-bridged gallium phthalocyanine dimer, and wherein there is formed in situ gallium alkoxide by the reaction of a gallium trichloride, and sodium alkoxide.

30. A process in accordance with claim 29 wherein said gallium alkoxide is gallium methoxide, and said sodium alkoxide is sodium methoxide.

31. A process for the preparation of alkoxy-bridged metallophthalocyanine dimers consisting of the reaction of a trivalent metal compound with ortho-phthalodinitrile or 1,3-diiminoisoindoline in the presence of a diol.

32. A process in accordance with claim 31 wherein the trivalent metal is aluminum, gallium indium, Mn(III), Fe(III), Co(III), Ni(III), Cr(III) or 33. A process in accordance with claim 31 wherein the trivalent metal compound is a metal alkoxide.

34. A process in accordance with claim 31 wherein the trivalent metal compound is an organic salt of said trivalent metal.

35. A process in accordance with claim 34 wherein the organic salt is triacetate, or triacetylacetonate.

36. A process in accordance with claim 33 wherein the trivalent metal alkoxide contains from 3 to about 54 carbon atoms.

* * * * *